(12) United States Patent
Møller et al.

(10) Patent No.: US 9,192,727 B2
(45) Date of Patent: Nov. 24, 2015

(54) INJECTION DEVICE WITH MODE LOCKING MEANS

(75) Inventors: Claus Schmidt Møller, Fredensborg (DK); Bennie Peder Smiszek Pedersen, Haslev (DK); Bo Kvolsbjerg, Helsingør (DK)

(73) Assignee: Novo Nordisk A/S, Bagsvaerd (DK)

( * ) Notice: Subject to any disclaimer, the term of this patent is extended or adjusted under 35 U.S.C. 154(b) by 815 days.

(21) Appl. No.: 12/300,675

(22) PCT Filed: May 3, 2007

(86) PCT No.: PCT/EP2007/054294
§ 371 (c)(1),
(2), (4) Date: Nov. 13, 2008

(87) PCT Pub. No.: WO2007/134954
PCT Pub. Date: Nov. 29, 2007

(65) Prior Publication Data
US 2009/0209920 A1 Aug. 20, 2009

Related U.S. Application Data

(60) Provisional application No. 60/810,610, filed on Jun. 2, 2006.

(30) Foreign Application Priority Data

May 18, 2006 (EP) .................................. 06010278

(51) Int. Cl.
*A61M 5/00* (2006.01)
*A61M 5/315* (2006.01)
(Continued)

(52) U.S. Cl.
CPC ............. *A61M 5/31553* (2013.01); *A61M 5/20* (2013.01); *A61M 5/31571* (2013.01); *A61M 5/24* (2013.01);
(Continued)

(58) Field of Classification Search
CPC .......... A61M 5/31553; A61M 5/3158; A61M 5/31571
USPC ......... 604/187, 207, 208, 211, 213, 218, 220, 604/224, 246
See application file for complete search history.

(56) References Cited

U.S. PATENT DOCUMENTS 854,399 A 5/1907 Bridge
2,392,196 A 2/1946 Smith
(Continued)

FOREIGN PATENT DOCUMENTS

AU 2003232576 1/2004
CA 2359375 7/2000
(Continued)

OTHER PUBLICATIONS

Abstract of AU2003232576 Published Jan. 19, 2004, 1 page.
(Continued)

*Primary Examiner* — Theodore Stigell
*Assistant Examiner* — Benjamin Koo
(74) *Attorney, Agent, or Firm* — Wesley Nicolas

(57) ABSTRACT

An injection device having a housing, a dose setting member being operable to set a desired dose, a piston rod adapted to cooperate with a piston to cause a set dose to be expelled, and a mode locking member. The mode locking member is adapted to be in a first extreme position and in a second extreme position. When the mode locking member is in the first extreme position the piston rod is prevented from cooperating with the piston, and when the mode locking member is in the second extreme position the dose setting member is prevented from being operated to set a dose. The mode locking member is adapted to be in the first extreme position during dose setting and the second extreme position during injection of a set dose.

22 Claims, 14 Drawing Sheets

(51) Int. Cl.
*A61M 5/20* (2006.01)
*A61M 5/24* (2006.01)
*A61M 5/31* (2006.01)

(52) U.S. Cl.
CPC ............ *A61M 5/3155* (2013.01); *A61M 5/3158* (2013.01); *A61M 5/31536* (2013.01); *A61M 5/31558* (2013.01); *A61M 5/31566* (2013.01); *A61M 5/31583* (2013.01); *A61M 5/31585* (2013.01); *A61M 2005/2407* (2013.01); *A61M 2005/2411* (2013.01); *A61M 2005/3125* (2013.01)

(56) References Cited

U.S. PATENT DOCUMENTS

| | | | |
|---|---|---|---|
| 2,956,563 A | 10/1960 | Sarnoff | |
| 3,110,310 A | 11/1963 | Cislak | |
| 3,115,135 A | 12/1963 | Sarnoff | |
| 3,144,178 A | 8/1964 | Sarnoff et al. | |
| 3,556,099 A | 1/1971 | Knight et al. | |
| 3,729,003 A | 4/1973 | Hurschman | |
| 3,880,162 A | 4/1975 | Simmons | |
| 3,944,843 A | 3/1976 | Vaz Martins | |
| 4,026,288 A | 5/1977 | Costa et al. | |
| 4,231,368 A | 11/1980 | Becker | |
| 4,275,727 A | 6/1981 | Keeri-Szanto | |
| 4,277,227 A | 7/1981 | Jenkins | |
| 4,298,000 A | 11/1981 | Thill et al. | |
| 4,300,554 A | 11/1981 | Hessberg et al. | |
| 4,313,439 A | 2/1982 | Babb et al. | |
| 4,314,556 A | 2/1982 | Ma | |
| 4,368,731 A | 1/1983 | Schramm | |
| RE31,315 E | 7/1983 | Jenkins et al. | |
| 4,393,723 A | 7/1983 | Brand | |
| 4,430,079 A | 2/1984 | Thill et al. | |
| 4,465,478 A | 8/1984 | Sabelman et al. | |
| 4,470,317 A | 9/1984 | Sabloewski et al. | |
| 4,493,704 A | 1/1985 | Beard et al. | |
| 4,498,904 A | 2/1985 | Turner et al. | |
| 4,515,584 A | 5/1985 | Abe et al. | |
| 4,568,335 A | 2/1986 | Updike et al. | |
| 4,584,439 A | 4/1986 | Paddock | |
| 4,585,439 A | 4/1986 | Michel | |
| 4,634,431 A | 1/1987 | Whitney et al. | |
| 4,676,122 A | 6/1987 | Szabo et al. | |
| 4,749,109 A | 6/1988 | Kamen | |
| 4,812,724 A | 3/1989 | Langer et al. | |
| 4,833,379 A | 5/1989 | Kaibel et al. | |
| 4,838,860 A | 6/1989 | Groshong et al. | |
| 4,865,591 A | 9/1989 | Sams | |
| 4,871,351 A | 10/1989 | Feingold | |
| 4,883,472 A | 11/1989 | Michel | |
| 4,893,291 A | 1/1990 | Bick et al. | |
| 4,898,578 A | 2/1990 | Rubalcaba | |
| 4,919,596 A | 4/1990 | Slate et al. | |
| 4,936,833 A | 6/1990 | Sams | |
| 4,950,246 A | 8/1990 | Muller | |
| 4,973,318 A | 11/1990 | Holm | |
| 4,988,337 A | 1/1991 | Ito | |
| 4,994,033 A | 2/1991 | Shockey et al. | |
| 4,998,922 A | 3/1991 | Kuracina et al. | |
| 5,000,744 A | 3/1991 | Hoffman et al. | |
| 5,002,537 A | 3/1991 | Hoffman et al. | |
| 5,011,479 A | 4/1991 | Le et al. | |
| 5,064,098 A | 11/1991 | Hutter et al. | |
| 5,078,698 A | 1/1992 | Stiehl et al. | |
| 5,104,388 A | 4/1992 | Quackenbus | |
| 5,112,317 A | 5/1992 | Michel | |
| 5,113,869 A | 5/1992 | Nappholz et al. | |
| 5,114,406 A | 5/1992 | Gabriel et al. | |
| 5,122,317 A | 6/1992 | Chen et al. | |
| 5,135,485 A | 8/1992 | Cohen et al. | |
| 5,154,698 A | 10/1992 | Compagnucci et al. | |
| 5,163,904 A | 11/1992 | Lampropoulos et al. | |
| 5,176,646 A | 1/1993 | Kuroda | |
| 5,207,752 A | 5/1993 | Sorenson et al. | |
| 5,221,268 A | 6/1993 | Barton et al. | |
| 5,226,342 A | 7/1993 | Panin | |
| 5,226,895 A | 7/1993 | Harris | |
| 5,226,896 A | 7/1993 | Harris | |
| 5,244,461 A | 9/1993 | Derlien | |
| 5,244,465 A | 9/1993 | Michel | |
| 5,246,417 A | 9/1993 | Haak et al. | |
| 5,257,987 A | 11/1993 | Athayde et al. | |
| 5,271,527 A | 12/1993 | Haber et al. | |
| 5,279,585 A | 1/1994 | Balkwill | |
| 5,279,586 A | 1/1994 | Balkwill | |
| 5,281,198 A | 1/1994 | Haber et al. | |
| 5,284,480 A | 2/1994 | Porter et al. | |
| 5,292,976 A | 3/1994 | Dessau et al. | |
| 5,295,976 A | 3/1994 | Harris | |
| 5,304,152 A | 4/1994 | Sams | |
| 5,308,340 A | 5/1994 | Harris | |
| 5,314,412 A | 5/1994 | Rex | |
| 5,318,540 A | 6/1994 | Athayde et al. | |
| 5,320,609 A | 6/1994 | Haber et al. | |
| 5,331,954 A | 7/1994 | Rex et al. | |
| 5,368,572 A | 11/1994 | Shirota | |
| 5,370,629 A | 12/1994 | Michel et al. | |
| 5,378,233 A | 1/1995 | Haber et al. | |
| 5,383,856 A | 1/1995 | Bersin | |
| 5,383,865 A | 1/1995 | Michel | |
| 5,440,976 A | 8/1995 | Giuliano et al. | |
| 5,445,606 A | 8/1995 | Haak et al. | |
| 5,447,150 A | 9/1995 | Bacon | |
| 5,478,316 A | 12/1995 | Bitdinger et al. | |
| 5,480,387 A | 1/1996 | Gabriel et al. | |
| 5,492,534 A | 2/1996 | Athayde et al. | |
| 5,496,286 A | 3/1996 | Stiehl et al. | |
| 5,505,697 A | 4/1996 | McKinnon, Jr. et al. | |
| 5,505,704 A | 4/1996 | Pawelka et al. | |
| 5,514,097 A | 5/1996 | Knauer | |
| 5,536,249 A | 7/1996 | Castellano et al. | |
| 5,546,932 A | 8/1996 | Galli | |
| 5,549,575 A | 8/1996 | Giambattista et al. | |
| 5,573,729 A | 11/1996 | Belgardt et al. | |
| 5,582,598 A | 12/1996 | Chanoch | |
| 5,584,815 A | 12/1996 | Pawelka et al. | |
| 5,591,136 A | 1/1997 | Gabriel | |
| 5,593,390 A | 1/1997 | Castellano et al. | |
| 5,599,314 A | 2/1997 | Neill | |
| 5,611,783 A | 3/1997 | Mikkelsen | |
| 5,611,784 A | 3/1997 | Barresi et al. | |
| 5,626,566 A | 5/1997 | Petersen et al. | |
| 5,628,309 A | 5/1997 | Brown | |
| 5,637,095 A | 6/1997 | Nason et al. | |
| 5,645,052 A | 7/1997 | Kersey | |
| 5,662,612 A | 9/1997 | Niehoff | |
| 5,674,204 A * | 10/1997 | Chanoch | 604/211 |
| 5,679,111 A | 10/1997 | Hertman et al. | |
| 5,681,285 A | 10/1997 | Ford et al. | |
| 5,685,864 A | 11/1997 | Shanley et al. | |
| 5,688,251 A | 11/1997 | Chanoch | |
| 5,709,662 A | 1/1998 | Olive et al. | |
| 5,716,990 A | 2/1998 | Bagshawe et al. | |
| 5,720,733 A | 2/1998 | Brown | |
| 5,725,508 A | 3/1998 | Chanoch | |
| 5,728,074 A | 3/1998 | Castellano et al. | |
| 5,728,559 A | 3/1998 | Nilsson et al. | |
| 5,741,211 A | 4/1998 | Renirie et al. | |
| 5,743,889 A | 4/1998 | Sams | |
| 5,755,692 A | 5/1998 | Manicom | |
| 5,782,633 A | 7/1998 | Muhlbauer | |
| 5,807,334 A | 9/1998 | Hodosh et al. | |
| 5,814,022 A | 9/1998 | Antanavich et al. | |
| 5,820,602 A | 10/1998 | Kovelman et al. | |
| 5,823,998 A | 10/1998 | Yamagata | |
| 5,827,232 A | 10/1998 | Chanoch | |
| 5,830,194 A | 11/1998 | Anwar et al. | |
| 5,843,036 A | 12/1998 | Olive et al. | |
| 5,879,360 A | 3/1999 | Crankshaw | |
| 5,879,630 A | 3/1999 | Lescouzeres et al. | |
| 5,882,718 A | 3/1999 | Pommer et al. | |

(56) References Cited

U.S. PATENT DOCUMENTS

| | | |
|---|---|---|
| 5,898,028 A | 4/1999 | Jensen et al. |
| 5,921,966 A | 7/1999 | Bendek et al. |
| 5,928,201 A | 7/1999 | Poulsen et al. |
| 5,933,671 A | 8/1999 | Stephany et al. |
| 5,938,642 A | 8/1999 | Burroughs et al. |
| 5,947,934 A | 9/1999 | Hansen |
| 5,951,530 A | 9/1999 | Steengaard et al. |
| 5,954,689 A | 9/1999 | Poulsen |
| 5,954,700 A | 9/1999 | Kovelman |
| 5,957,889 A | 9/1999 | Poulsen et al. |
| 5,961,496 A | 10/1999 | Nielsen et al. |
| 5,971,963 A | 10/1999 | Choi |
| 5,980,491 A | 11/1999 | Hansen |
| 5,984,900 A | 11/1999 | Mikkelsen |
| 5,989,221 A | 11/1999 | Hjertman |
| 5,998,989 A | 12/1999 | Lohberg |
| 6,003,736 A | 12/1999 | Ljunggren |
| 6,004,297 A | 12/1999 | Steenfeldt-Jensen et al. |
| 6,010,485 A | 1/2000 | Buch-Rasmussen et al. |
| 6,019,745 A | 2/2000 | Gray |
| 6,033,376 A | 3/2000 | Rockley |
| 6,033,377 A | 3/2000 | Rasmussen et al. |
| 6,036,675 A | 3/2000 | Thorne et al. |
| 6,048,336 A | 4/2000 | Gabriel |
| 6,074,372 A | 6/2000 | Hansen |
| 6,083,197 A | 7/2000 | Umbaugh |
| 6,086,567 A | 7/2000 | Kirchhofer et al. |
| 6,096,010 A | 8/2000 | Walters |
| 6,110,148 A | 8/2000 | Brown et al. |
| 6,110,149 A | 8/2000 | Klitgaard et al. |
| 6,129,080 A | 10/2000 | Pitcher et al. |
| 6,146,361 A | 11/2000 | DiBiasi et al. |
| 6,159,161 A | 12/2000 | Hodosh |
| 6,161,364 A | 12/2000 | Kolberg |
| 6,193,698 B1 | 2/2001 | Kirchhofer et al. |
| 6,221,046 B1 | 4/2001 | Burroughs et al. |
| 6,221,053 B1 | 4/2001 | Walters et al. |
| 6,231,540 B1 | 5/2001 | Smedegaard |
| 6,235,004 B1 | 5/2001 | Steenfeldt-Jensen et al. |
| 6,245,046 B1 | 6/2001 | Sibbitt |
| 6,248,090 B1 | 6/2001 | Jensen et al. |
| 6,248,095 B1 | 6/2001 | Giambattista |
| 6,258,062 B1 | 7/2001 | Thielen et al. |
| 6,268,722 B1 | 7/2001 | Kogure et al. |
| 6,269,340 B1 | 7/2001 | Ford et al. |
| 6,277,097 B1 | 8/2001 | Mikkelsen et al. |
| 6,277,098 B1 | 8/2001 | Klitmose et al. |
| 6,281,225 B1 | 8/2001 | Hearst et al. |
| 6,283,941 B1 | 9/2001 | Schoenfeld et al. |
| 6,287,283 B1 | 9/2001 | Ljunggreen et al. |
| 6,302,869 B1 | 10/2001 | Klitgaard |
| 6,312,413 B1 | 11/2001 | Jensen et al. |
| 6,340,357 B1 | 1/2002 | Poulsen et al. |
| 6,364,860 B1 | 4/2002 | Steck et al. |
| 6,379,339 B1 | 4/2002 | Klitgaard et al. |
| 6,383,167 B2 | 5/2002 | Kirchhofer et al. |
| 6,391,005 B1 | 5/2002 | Lum et al. |
| 6,419,661 B1 | 7/2002 | Kuhr et al. |
| 6,514,230 B1 | 2/2003 | Munk et al. |
| 6,537,251 B2 | 3/2003 | Klitmose |
| 6,547,755 B1 | 4/2003 | Lippe et al. |
| 6,547,763 B2 | 4/2003 | Steenfeldt-Jensen et al. |
| 6,547,764 B2 | 4/2003 | Larsen et al. |
| 6,562,011 B1 | 5/2003 | Buch-Rasmussen et al. |
| 6,569,126 B1 | 5/2003 | Poulsen et al. |
| 6,582,404 B1 | 6/2003 | Klitgaard et al. |
| 6,585,698 B1 | 7/2003 | Packman et al. |
| 6,599,272 B1 | 7/2003 | Hjertman et al. |
| 6,605,067 B1 | 8/2003 | Larsen |
| 6,613,019 B2 | 9/2003 | Munk |
| 6,663,602 B2 | 12/2003 | Moller |
| 6,666,849 B1 | 12/2003 | Marshall et al. |
| 6,673,033 B1 | 1/2004 | Sciulli et al. |
| 6,692,472 B2 | 2/2004 | Hansen et al. |
| 6,699,224 B2 | 3/2004 | Kirchhofer et al. |
| 6,716,198 B2 | 4/2004 | Larsen |
| 6,726,661 B2 | 4/2004 | Munk et al. |
| 6,752,798 B2 | 6/2004 | McWethy et al. |
| 6,770,288 B2 | 8/2004 | Duirs |
| 6,796,970 B1 | 9/2004 | Klitmose et al. |
| 6,852,404 B2 | 2/2005 | Kuwajima et al. |
| 6,887,238 B2 | 5/2005 | Jahns et al. |
| 6,893,415 B2 | 5/2005 | Madsen et al. |
| 6,899,698 B2 | 5/2005 | Sams |
| 6,899,699 B2 | 5/2005 | Enggaard |
| 6,945,961 B2 | 9/2005 | Miller et al. |
| 7,008,399 B2 | 3/2006 | Larsen et al. |
| 7,080,936 B1 | 7/2006 | Simpson |
| 7,090,662 B2 | 8/2006 | Wimpenny et al. |
| 7,094,221 B2 | 8/2006 | Veasey et al. |
| 7,104,972 B2 | 9/2006 | Moller |
| 7,133,329 B2 | 11/2006 | Skyggebjerg |
| 7,175,055 B2 | 2/2007 | Hansen et al. |
| 7,195,609 B2 | 3/2007 | Huegli |
| 7,195,616 B2 | 3/2007 | Diller et al. |
| 7,241,278 B2 | 7/2007 | Moller |
| 7,500,966 B2 | 3/2009 | Hommann |
| 7,678,084 B2 | 3/2010 | Judson et al. |
| 7,686,786 B2 | 3/2010 | Moller et al. |
| 7,704,238 B2 | 4/2010 | Diller et al. |
| 7,771,399 B2 | 8/2010 | Burren et al. |
| 8,048,037 B2 | 11/2011 | Kohlbrenner et al. |
| 8,202,256 B2 | 6/2012 | Moller |
| 8,206,361 B2 | 6/2012 | Moller |
| 8,267,899 B2 | 9/2012 | Moller |
| 2001/0034506 A1 | 10/2001 | Hirschman et al. |
| 2001/0053893 A1 | 12/2001 | Larsen |
| 2002/0002326 A1 | 1/2002 | Causey, III et al. |
| 2002/0002354 A1 | 1/2002 | Vetter et al. |
| 2002/0007154 A1 | 1/2002 | Hansen et al. |
| 2002/0016571 A1 | 2/2002 | Kirchhofer et al. |
| 2002/0020654 A1 | 2/2002 | Eilersen |
| 2002/0049415 A1 | 4/2002 | Fukuda |
| 2002/0052578 A1 | 5/2002 | Moller |
| 2002/0077852 A1 | 6/2002 | Ford et al. |
| 2002/0107486 A1 | 8/2002 | Munk |
| 2002/0120235 A1 | 8/2002 | Enggaard |
| 2002/0165500 A1 | 11/2002 | Bechtold et al. |
| 2002/0173752 A1 | 11/2002 | Polzin |
| 2002/0188250 A1 | 12/2002 | Landau et al. |
| 2003/0009133 A1 | 1/2003 | Ramey |
| 2003/0039679 A1 | 2/2003 | Duirs |
| 2003/0040715 A1 | 2/2003 | D'Antonio et al. |
| 2003/0050609 A1 | 3/2003 | Sams |
| 2003/0073954 A1 | 4/2003 | Moberg et al. |
| 2003/0114800 A1 | 6/2003 | Veasey et al. |
| 2003/0172924 A1 | 9/2003 | Staniforth et al. |
| 2003/0176871 A1 | 9/2003 | Pavlov et al. |
| 2003/0216663 A1 | 11/2003 | Willuhn et al. |
| 2003/0233075 A1 | 12/2003 | Huegli et al. |
| 2004/0010204 A1 | 1/2004 | Weber et al. |
| 2004/0024361 A1 | 2/2004 | Fago |
| 2004/0051368 A1 | 3/2004 | Caputo et al. |
| 2004/0054326 A1 | 3/2004 | Hommann et al. |
| 2004/0059299 A1 | 3/2004 | Moller |
| 2004/0097879 A1 | 5/2004 | Woolston |
| 2004/0108339 A1 | 6/2004 | Hansen et al. |
| 2004/0158304 A1 | 8/2004 | Cory et al. |
| 2004/0171983 A1 | 9/2004 | Sparks et al. |
| 2004/0186431 A1 | 9/2004 | Graf et al. |
| 2004/0207385 A1 | 10/2004 | Gafner et al. |
| 2004/0210199 A1 | 10/2004 | Atterbury et al. |
| 2004/0230157 A1 | 11/2004 | Perry et al. |
| 2004/0236282 A1 | 11/2004 | Braithwaite |
| 2004/0249348 A1 | 12/2004 | Wimpenny et al. |
| 2004/0260247 A1 | 12/2004 | Veasey et al. |
| 2004/0267207 A1 | 12/2004 | Veasey et al. |
| 2004/0267208 A1 | 12/2004 | Veasey et al. |
| 2005/0004529 A1 | 1/2005 | Veasey et al. |
| 2005/0019400 A1 | 1/2005 | Deveney et al. |
| 2005/0033244 A1 | 2/2005 | Veasey et al. |
| 2005/0055011 A1 | 3/2005 | Enggaard |
| 2005/0197625 A1 | 9/2005 | Haueter et al. |
| 2005/0205083 A1 | 9/2005 | Staniforth et al. |

(56) References Cited

U.S. PATENT DOCUMENTS

| | | |
|---|---|---|
| 2005/0209570 A1 | 9/2005 | Moller |
| 2005/0268915 A1 | 12/2005 | Wassenaar et al. |
| 2006/0118612 A1 | 6/2006 | Christoffersen et al. |
| 2006/0258988 A1 | 11/2006 | Keitel et al. |
| 2006/0264838 A1 | 11/2006 | Volckmann |
| 2007/0093761 A1 | 4/2007 | Veasey |
| 2007/0167916 A1 | 7/2007 | Lee et al. |
| 2007/0244445 A1 | 10/2007 | Moller |
| 2007/0265568 A1 | 11/2007 | Tsals et al. |
| 2008/0065026 A1 | 3/2008 | Moller |
| 2008/0221530 A1 | 9/2008 | Glejbol et al. |
| 2008/0281275 A1 | 11/2008 | Moller |
| 2008/0306445 A1 | 12/2008 | Burren et al. |
| 2008/0312592 A1 | 12/2008 | Barrow-Williams et al. |
| 2009/0043264 A1 | 2/2009 | Glejbol et al. |
| 2009/0062748 A1 | 3/2009 | Moller et al. |
| 2013/0204197 A1 | 8/2013 | Bicknell et al. |

FOREIGN PATENT DOCUMENTS

| | | |
|---|---|---|
| CA | 2359375 A1 | 7/2000 |
| CN | 1214292 A | 4/1999 |
| DE | 3048135 | 7/1982 |
| DE | 3236374 | 4/1984 |
| DE | 3609555 | 9/1987 |
| DE | 3638984 | 5/1988 |
| DE | 3923079 | 1/1991 |
| DE | 4223958 | 1/1993 |
| DE | 4419235 | 12/1995 |
| DE | 19503230 | 8/1996 |
| DE | 19838760 | 4/2000 |
| DE | 29907880 | 9/2000 |
| DE | 10103287 | 8/2001 |
| DE | 20209051 U1 | 4/2003 |
| DE | 10201875 | 5/2003 |
| DE | 10229122 | 2/2004 |
| DE | 20317377 | 4/2005 |
| DE | 102004046003 | 3/2006 |
| DK | 200100240 | 2/2001 |
| EA | 008160 | 4/2007 |
| EP | 15617 | 9/1980 |
| EP | 017318 | 10/1980 |
| EP | 0064858 | 11/1982 |
| EP | 327810 | 8/1989 |
| EP | 327810 A2 | 8/1989 |
| EP | 327910 A2 | 8/1989 |
| EP | 338806 | 10/1989 |
| EP | 0362484 | 4/1990 |
| EP | 387854 | 9/1990 |
| EP | 422482 | 4/1991 |
| EP | 454331 | 10/1991 |
| EP | 327910 | 4/1992 |
| EP | 498737 | 8/1992 |
| EP | 879610 | 8/1992 |
| EP | 554996 | 8/1993 |
| EP | 594349 | 4/1994 |
| EP | 608343 | 9/1994 |
| EP | 615762 | 9/1994 |
| EP | 679440 | 11/1995 |
| EP | 679440 A1 | 11/1995 |
| EP | 702970 | 3/1996 |
| EP | 1000631 | 10/1997 |
| EP | 554995 | 12/1997 |
| EP | 0 673 482 | 4/1998 |
| EP | 295075 | 12/1998 |
| EP | 897728 | 2/1999 |
| EP | 897729 A2 | 2/1999 |
| EP | 0937471 | 8/1999 |
| EP | 0937472 | 8/1999 |
| EP | 956873 A2 | 11/1999 |
| EP | 1351732 | 1/2001 |
| EP | 1074273 | 2/2001 |
| EP | 1095668 | 5/2001 |
| EP | 0747391 | 3/2004 |
| EP | 1462134 | 9/2004 |
| EP | 937476 | 1/2005 |
| EP | 1541185 | 6/2005 |
| EP | 1557189 | 7/2005 |
| EP | 1557189 A1 | 7/2005 |
| EP | 1568389 | 8/2005 |
| EP | 1304129 | 11/2005 |
| EP | 1610848 | 1/2006 |
| EP | 1645301 | 4/2006 |
| EP | 1723977 | 11/2006 |
| EP | 1728529 | 12/2006 |
| EP | 1782853 | 5/2007 |
| EP | 1819382 | 8/2007 |
| EP | 2000161 | 12/2008 |
| EP | 2019701 A1 | 2/2009 |
| EP | 2373361 A1 | 10/2011 |
| FR | 2583291 | 12/1986 |
| FR | 2622457 | 5/1989 |
| FR | 2697434 | 5/1994 |
| FR | 2697434 A1 | 5/1994 |
| FR | 2740345 | 4/1997 |
| FR | 2767479 | 2/1999 |
| FR | 2857654 | 1/2005 |
| GB | 664044 | 1/1952 |
| GB | 2091107 | 7/1982 |
| GB | 2153445 | 8/1985 |
| GB | 2229497 | 9/1990 |
| GB | 2309644 | 8/1997 |
| IN | 165367 | 3/1986 |
| JP | 56-163486 | 12/1981 |
| JP | 57-000033 | 1/1982 |
| JP | 01-035671 A | 2/1989 |
| JP | 01-100495 | 4/1989 |
| JP | 64-035671 | 6/1989 |
| JP | 02071758 A | 3/1990 |
| JP | 02-126184 | 5/1990 |
| JP | 02-182267 | 7/1990 |
| JP | 4-224764 | 8/1992 |
| JP | 04256757 A | 9/1992 |
| JP | 4-507059 | 12/1992 |
| JP | 05-337179 | 12/1993 |
| JP | 06-055644 | 1/1994 |
| JP | 7-500039 | 3/1994 |
| JP | 06-034825 | 10/1994 |
| JP | 06-296691 | 10/1994 |
| JP | 09166474 | 6/1997 |
| JP | 11511364 | 10/1999 |
| JP | 3017167 | 11/1999 |
| JP | 2000237308 | 9/2000 |
| JP | 2002503122 | 1/2002 |
| JP | 2003284777 | 10/2003 |
| JP | 2004533285 A | 11/2004 |
| JP | 2005536300 A | 12/2005 |
| JP | 2006250582 | 9/2006 |
| JP | 2007-509662 | 4/2007 |
| JP | 2008-528071 A | 7/2008 |
| JP | 2008-196696 A | 8/2008 |
| PL | 1804865 | 10/2005 |
| RU | 2111019 | 5/1997 |
| RU | 2111019 C1 | 5/1997 |
| RU | 2254878 C2 | 6/2005 |
| SU | 1528330 A3 | 12/1989 |
| WO | WO8502256 | 5/1985 |
| WO | WO 8702895 | 5/1987 |
| WO | WO 8907463 | 8/1989 |
| WO | 90/09202 | 8/1990 |
| WO | WO 9009202 | 8/1990 |
| WO | WO 9110460 | 7/1991 |
| WO | WO9110677 | 7/1991 |
| WO | 91/14467 A1 | 10/1991 |
| WO | WO 9114467 | 10/1991 |
| WO | WO9301573 | 1/1993 |
| WO | WO 93/03780 | 3/1993 |
| WO | WO 93/07922 | 4/1993 |
| WO | WO 94/12228 | 6/1994 |
| WO | 95/21645 A1 | 8/1995 |
| WO | WO9524233 | 9/1995 |
| WO | WO 96/07443 | 3/1996 |
| WO | WO 9626754 | 9/1996 |

(56) References Cited

FOREIGN PATENT DOCUMENTS

| | | |
|---|---|---|
| WO | WO96/32973 | 10/1996 |
| WO | WO 96/38190 | 12/1996 |
| WO | WO 97/10865 | 3/1997 |
| WO | WO 9707841 | 3/1997 |
| WO | WO9730742 | 8/1997 |
| WO | WO9734919 | 9/1997 |
| WO | WO 9736626 | 10/1997 |
| WO | WO 9810813 | 3/1998 |
| WO | 9856439 | 12/1998 |
| WO | WO 9856436 | 12/1998 |
| WO | WO 9857688 | 12/1998 |
| WO | WO9907425 | 2/1999 |
| WO | WO9915214 | 4/1999 |
| WO | WO 9916487 | 4/1999 |
| WO | WO 9921598 | 5/1999 |
| WO | WO 99/38554 | 8/1999 |
| WO | WO 9948546 | 9/1999 |
| WO | WO9965548 | 12/1999 |
| WO | WO0037129 | 6/2000 |
| WO | WO 00/51668 | 9/2000 |
| WO | WO 01/10484 | 2/2001 |
| WO | WO0126710 | 4/2001 |
| WO | WO 01/30425 | 5/2001 |
| WO | WO0172361 | 10/2001 |
| WO | WO0205876 | 1/2002 |
| WO | WO0224257 | 3/2002 |
| WO | WO 02/053214 | 7/2002 |
| WO | WO02064196 | 8/2002 |
| WO | 02/076537 | 10/2002 |
| WO | WO 02/076535 | 10/2002 |
| WO | WO 02076536 | 10/2002 |
| WO | 02/092153 | 11/2002 |
| WO | WO 02092153 | 11/2002 |
| WO | 03/057286 A1 | 7/2003 |
| WO | WO03057283 | 7/2003 |
| WO | WO03063680 | 8/2003 |
| WO | WO9733638 | 9/2003 |
| WO | WO 03/080160 | 10/2003 |
| WO | WO03099357 | 12/2003 |
| WO | WO 2004/002556 | 1/2004 |
| WO | WO 2004004825 | 1/2004 |
| WO | WO 2004/007002 | 1/2004 |
| WO | 2004020026 | 3/2004 |
| WO | WO 2004/024218 | 3/2004 |
| WO | WO 2004/028598 | 4/2004 |
| WO | WO 2006/045529 | 4/2004 |
| WO | WO 2004035113 | 4/2004 |
| WO | WO 2004/078240 | 9/2004 |
| WO | WO 2004/078242 | 9/2004 |
| WO | WO 2004078239 | 9/2004 |
| WO | WO 2004/078241 | 9/2004 |
| WO | WO2004080306 | 9/2004 |
| WO | WO2004084795 | 10/2004 |
| WO | 2004/093940 A2 | 11/2004 |
| WO | WO2004095379 | 11/2004 |
| WO | WO 2005/018721 | 3/2005 |
| WO | WO 2005037352 | 4/2005 |
| WO | WO 2005/046770 | 5/2005 |
| WO | WO2005089835 | 9/2005 |
| WO | WO2005097233 | 10/2005 |
| WO | WO2005097240 | 10/2005 |
| WO | 20051102421 A1 | 11/2005 |
| WO | 2006/026754 A2 | 3/2006 |
| WO | 2006/037434 A1 | 4/2006 |
| WO | 2006040296 A2 | 4/2006 |
| WO | WO 2006/039930 | 4/2006 |
| WO | 2006045526 A1 | 5/2006 |
| WO | WO 2006/045528 | 5/2006 |
| WO | WO2006045425 | 5/2006 |
| WO | WO2006045525 | 5/2006 |
| WO | WO 2006/069454 | 7/2006 |
| WO | WO2006076921 | 7/2006 |
| WO | WO2006116997 | 11/2006 |
| WO | WO 2006/128794 | 12/2006 |
| WO | 2007021195 A1 | 2/2007 |
| WO | WO 2007/030957 | 3/2007 |
| WO | WO2007041843 | 4/2007 |
| WO | 2007063342 A1 | 6/2007 |
| WO | 2007104636 A1 | 9/2007 |
| WO | WO2007107558 | 9/2007 |
| WO | WO2007107561 | 9/2007 |
| WO | WO 2007/134954 | 11/2007 |
| WO | 2008/003130 A1 | 1/2008 |
| WO | WO 2008/037801 | 4/2008 |
| WO | WO2008057223 | 5/2008 |
| WO | 2010046394 A1 | 4/2010 |
| WO | 2010089418 A2 | 8/2010 |
| WO | 2011025448 A1 | 3/2011 |
| WO | 2011136718 A1 | 11/2011 |

OTHER PUBLICATIONS

English Translation for DE3609555 Published Sep. 24, 1987, 2 pages.
English Translation for EP679440 Published Nov. 2, 1995, 4 pages.
Machine Translation of FR2583291TX Published Dec. 19, 1986, 3 pages.
English Abstract of FR2767479 Published Feb. 26, 1999, 4 pages.
English Abstract for JP 2000237308 Published Sep. 5, 2000, 1 page.
English Abstract for JP 2003284777 Published Oct. 7, 2003, 1 page.
English Abtsract of JP4-507059 Published Dec. 10, 1992, 1 page.
English Abstract for JP2005337179 Published Dec. 21, 1993, 2 pages.
English Abstract of JP06-296691 Published Oct. 25, 1994, 4 pages.
English Abstract for RU2111019 Published May 22, 1997, 1 pages.
Office Action Mailed Dec. 27, 2010 in U.S. Appl. No. 12/442,168, filed Mar. 20, 2009 by Moller et al., (8 pages).
Final Rejection Mailed on Dec. 13, 2010 in U.S. Appl. No. 12/571,721, filed Oct. 1, 2009 by Glejbol et al., (9 pages).
Rose, Keith et al., Bioconjugate Chemistry, "Natural Peptides as Building Blocks for the Synthesis of Large Protein-Like Molecules With Hydrazone and Oxime Linkages", 1996, vol. 7, 2, pp. 552-556.
Yurkovetskiy, A. et al., Biomacromolecules., "Fully Degradable Hydrophilic Polyals for Protein Modification", 2005, vol. 6, 5, pp. 2648-2658.
Answer in *Novo Nordisk A/S v. Sanofi-Aventis U.S. LLC and Sanofi-Aventis* downloaded from PACER on Feb. 29, 2008.
Complaint in *Novo Nordisk A/S v. Sanofi-Aventis U.S. LLC and Sanofi-Aventis* downloaded from PACER on Feb. 29, 2008.
Declaration of Benard Sams in *Novo Nordisk A/S v. Sanofi-Aventis U.S. LLC and Sanofi-Aventis* downloaded from PACER on Feb. 29, 2008.
Opinion of US District Court for the District of NJ in *Novo Nordisk A/S v. Sanofi-Aventis U.S. LLC and Sanofi-Aventis*, Denying motion of a preliminary injunction, entered Feb. 20, 2008.
Reissue U.S. Appl. No. 10/442,855 File history.
Reissue U.S. Appl. No. 10/960,900 File history.
Reissue U.S. Appl. No. 11/121,331 File History.
Reissue U.S. Appl. No. 11/640,610 File History.
English language abstract of French Patent No. 2697434, published on May 6, 1994 obtained from Derwent Patent Database.
English language abstract of German Patent No. 3048135, published on Jul. 15, 1982 obtained from Derwent Patent Database.
Written Opinion issued in connection with counterpart PCT Appliaction No. PCT/EP2006/061748, mailed Nov. 8, 2006.
Final Action in U.S. Appl. No. 11/931,010, mailed from the USPTO on Jan. 15, 2010.
Office Action in U.S. Appl. No. 11/931,010, mailed from the USPTO on Apr. 2, 2009.
Final Action in U.S. Appl. No. 11/122,289, mailed from the USPTO on Nov. 5, 2009.
Final Action in U.S. Appl. No. 11/765,789, mailed from the USPTO on Nov. 5, 2009.
Office Action in U.S. Appl. No. 11/765,789, mailed from the USPTO on Dec. 17, 2008.
Office Action in U.S. Appl. No. 11/765,789, mailed from the USPTO on Mar. 14, 2008.
Final Action in U.S. Appl. No. 11/930,926, mailed from the USPTO on Jan. 15, 2010.

(56) References Cited

OTHER PUBLICATIONS

Office Action in U.S. Appl. No. 11/930,926, mailed from the USPTO on Apr. 2, 2009.
English Abstract of DE10201875 Published May 22, 2003.
English Abstract of DE102004046003 Published Mar. 30, 2006.
English Abstract of DE19503230 Published Aug. 8, 1996.
English Abstract of DE 19838760 Dated Apr. 20, 2000.
English Abstract of DE3236374 Published Apr. 5, 1984.
English Abstract of DE3923079 Published Jan. 24, 1991.
English Abstract for DE4419235 Publihed Dec. 7, 1995.
English Abstract of EP387854 Published Sep. 19, 1990.
English Abstract of EP422482 Published Apr. 17, 1991.
English Abstract of FR2622457 Published May 5, 1989.
English Abstract of FR2740345 Publisiied Apr. 30, 1997.
English Abstract of IN165367 Published Mar. 20, 1986.
English Abstract of JP01-100495 Published Apr. 18, 1989.
English Abstract of JP02-126184 Published May 15, 1990.
English Abstract of JP02-182267 Published Jul. 16, 1990.
English Abstract of JP64-035671 Published Jun. 2, 1989.
English Abstract of JP06-034825 Published Oct. 2, 1994.
English Abstract of JP06-055644 Published Jan. 3, 1994.
Machine Translation of JP09166474 Published Jun. 24, 1997.
English Abstract of JP2006250582 Published Sep. 21, 2006.
English Abstract of JP3017167 Published Nov. 30, 1999.
English Abstract of JP56-163486 Published Dec. 16, 1981.
English Abstract of JP57-000033 Published Jan. 5, 1982.
English Abstract of JP 7-500039 Published Mar. 14, 1994.
Annersten, M. et al., Insulin Pens Dribble From the Tip of the Needle After Injection, Practical Diabetes Int., vol. 17(4), pp. 109-111 (2000).
Beckmann, Sensors, Memory, Circuits, Polyapply Newsletter, vol. 1(3), (2006).
Chia Kai Su et al, Process Biochemistry, 2006, vol. 41, Part 2, pp. 257-263.
Common Insulin Injection Challenges: http://www.bd.com/us/diabetes/page.aspx?cat=7001&id=7265, Jun. 30, 2010.
Dennison, Clive et al, Protein Expression and Purification, 2004, vol. 11, Part 2, pp. 149-161.
Fransson et al, Pharmaceutical Research, 1997, vol. 14, Part 5, pp. 606-612.
Gnanalingham, M.G. et al., Accuracy and Reproducibility of Low Dose Insulin Administration Using Pen-Injectors and Syringes, Downloaded From ABC.BMJ.com on Jan. 9, 2008.
Leonil et al, Enzyme and Microbiol Technology, 1994, vol. 16, Part 7, pp. 591-595.
Paule, B.J.A. et al, Protein Expression and Purification, 2004, vol. 34, Part 2, pp. 311-316.

Search Report Issued in Connection With PCT Appln. No. PCT/EP2007/052630, Mailed Nov. 12, 2007.
Search Report Issued in Connection With European Appln No. 06005602.5, Mailed Oct. 16, 2006.
Notice of Opposition by Owen Mumford (UK), 2006.
Notice of Opposition by Genentech (USA), 2006.
Notice of Opposition by Techpharma (CH) Including English Translation, 2006.
Opposition in Related European Patent Application EP 02711784.5 of Sep. 19, 2008.
Office Action Mailed on Sep. 15, 2004 in U.S. Appl. No. 10/646,295, filed Aug. 22, 2003 by Hansen et al.
Final Office Action Mailed on Feb. 8, 2005 in U.S. Appl. No. 10/646,295, filed Aug. 22, 2003 by Hansen et al.
Advisory Action Mailed Jul. 1, 2005 in U.S. Appl. No. 10/646,295, filed Aug. 22, 2003 by Hansen et al.
Office Action Mailed on Aug. 29, 2005 in U.S. Appl. No. 10/646,295, filed Aug. 22, 2003 by Hansen et al.
Final Office Action Mailed on Apr. 14, 2006 in U.S. Appl. No. 10/646,295, filed Aug. 22, 2003 by Hansen et al.
Notice of Allowance Mailed on Sep. 26, 2006 in U.S. Appl. No. 10/646,295, filed Aug. 22, 2003 by Hansen et al.
Notice of Allowance Mailed on Apr. 23, 2007 in U.S. Appl. No. 10/667,040, filed Sep. 22, 2003 by Moller et al.
Office Action Mailed on Dec. 15, 2008 in U.S. Appl. No. 11/122,289, filed May 4, 2005 by Moller et al.
Advisory Action Mailed on Mar. 25, 2010 in U.S. Appl. No. 11/122,289, filed May 4, 2005 by Moller et al.
Office Action Mailed on Jan. 8, 2009 in U.S. Appl. No. 11/911,869, filed Oct. 18, 2007 by Glejbol et al.
Final Office Action Mailed on Sep. 29, 2009 in U.S. Appl. No. 11/911,869, filed Oct. 18, 2007 by Glejbol et al.
Abandonment Mailed on Oct. 8, 2009 in U.S. Appl. No. 11/911,869, filed Oct. 18, 2007 by Glejbol et al.
Office Action Mailed on Apr. 1, 2009 in U.S. Appl. No. 11/911,871, filed October 18, 2007 by Glejbol et al.
Abandonment Mailed on Nov. 6, 2009 in U.S. Appl. No. 11/911,871, filed October 18, 2007 by Glejbol et al.
Non-Final Rejection Mailed on June 8, 2010 in U.S. Appl. No. 12/571,721, filed October 1, 2009 by Glejbol et al.
Non-Final Rejection of Oct. 7, 2008 in U.S. Appl. No. 10/508,104 (US Patent No. 7,678,084; Issue Date Mar. 16, 2010) filed Sep. 15, 2004; First Named Inventor: Jared Alden Judson.
Non-Final Rejection of Mar. 19, 2009 in U.S. Appl. No. 10/508,104 (US Patent No. 7,678,084; Issue Date Mar. 16, 2010) filed Sep. 15, 2004; first Named Inventor: Jared Alden Judson.
File history of U.S. Appl. No. 10/610.926 which is owned by the same assignee as U.S. Appl. No. 11/765,789, filed Jun. 20, 2007 by Moller et al.

\* cited by examiner

INJECTION DEVICE WITH MODE LOCKING MEANS

CROSS-REFERENCE TO RELATED APPLICATIONS

This application is a 35 U.S.C. §371 national stage application of International Patent Application PCT/EP2007/054294 (published as WO 2007/134954), filed May 3, 2007, which claimed priority of European Patent Application 06010278.7, filed May 18, 2006; this application further claims priority under 35 U.S.C. §119 of U.S. Provisional Application 60/810,610, filed Jun. 2, 2006.

FIELD OF THE INVENTION

The present invention relates to an injection device, in particular an injection device which is suitable for use for self-medication, e.g. for administering insulin to persons with diabetes, or for administering growth hormone. More particularly, the present invention relates to an injection device as defined above and which is capable of preventing unintended expelling of liquid drug during dose setting, and unintended movement of a dose setting mechanism during injection of a set dose.

BACKGROUND OF THE INVENTION

When using injection devices as defined above, a desired dose is normally set by means of a dose setting mechanism. When the dose has been set, an injection needle is positioned at a desired injection position, and the set dose is injected by means of an injection mechanism, normally including a manually operable injection button and a piston rod cooperating with a piston of a cartridge containing the drug to be injected.

If it is possible for the piston rod to move in a distal direction during setting of a dose, there is a risk that liquid drug is accidentally spilled during dose setting. Furthermore, if it is possible for the piston rod to move in a proximal direction during dose setting, the pressure applied to the piston from the piston rod may decrease, possibly even forming a gap between the piston and the piston rod, and thereby there is a risk that blood is sucked into the cartridge when the injection needle of the device is subsequently inserted at the injection site. Furthermore, if it is possible for the dose setting mechanism to move during injection of an initially set dose, the set dose may accidentally be increased or decreased during the injection, and the actually injected dose may thereby be unknown. This is very undesirable. It is therefore desirable to be able to prevent such undesired movements of the piston rod and the dose setting mechanism, respectively.

Attempts have been made to solve the problem described above in injection devices of the kind having a cylindrical scale drum with a helical spiral of numbers written thereon. When a dose is set in such an injection device the cylindrical scale drum is dialled outwards, and a number corresponding to the set dose will show in a window on the injection device. US 2004/0059299 discloses an injection device of this kind. The injection device is provided with a dose setting element which, during dose setting, is coupled rotationally as well as axially to the scale drum. During injection the dose setting member is prevented from rotating. At the same time the dose setting element is coupled to a dose rod which can be rotated along a piston rod via a gearwheel providing a gearing corresponding to the pitch of the scale drum. Since the dose setting element and the scale drum are axially coupled during dose setting, the dose rod is rotated in a controlled manner, thereby preventing the piston rod from moving during dose setting. Since the dose setting element is prevented from rotating during injection, the dose rod is pushed back without performing a rotational movement, thereby causing an advancing movement of the piston rod.

EP 1 304 129 discloses a medication dispensing device including a lockout mechanism that prevents the dial from being depressed during dosing. The apparatus includes a drive assembly mounted to the housing and manually advanceable in the housing between a dose setting position and an injection position for manually moving the drive stem to drive the piston within a container. The drive assembly is locked from movement with respect to the housing along the axis of ejection while in the dose setting position. A disengaging device is secured to at least one of the drive assembly and the housing to unlock the drive assembly from the housing to enable the drive assembly to be axially advanceable with respect to the housing to move the drive assembly from the dose setting position to the injection position.

The injection device disclosed in EP 1 304 129 is also of the kind having a cylindrical scale drum, and the mechanism described above is connected to the scale drum.

It is a disadvantage that the mechanism which prevents undesired movements of the piston rod during dose setting is connected to the scale drum, since the mechanism therefore can not readily be applied to injection devices which are not provided with a cylindrical scale drum. Furthermore, it is sometimes desirable to design an injection device without such a cylindrical scale drum, e.g. in order to use the space occupied by a scale drum for other purposes, e.g. additional electronics for controlling the injection device, or simply because a different counter mechanism is desired. However, it is still desirable to be able to overcome the problems outlined above in such an injection device.

SUMMARY OF THE INVENTION

It is, thus, an object of the invention to provide an injection device in which it is possible to prevent undesired spilling of drug during dose setting, as well as undesired movements of the dose setting means during injection.

It is a further object of the invention to provide a relatively flat injection device which is capable of preventing undesired spilling of drug during dose setting, as well as undesired movements of the dose setting means during injection.

It is an even further object of the invention to provide an injection device without a cylindrical scale drum, and which is capable of preventing undesired spilling of drug during dose setting, as well as undesired movements of the dose setting means during injection.

According to the invention the above and other objects are fulfilled by providing an injection device comprising:
 a housing,
 a dose setting member being operable to set a desired dose,
 a piston rod adapted to cooperate with a piston to cause a set dose to be expelled from the injection device,
 mode locking means adapted to be in a first extreme position, in which the piston rod is prevented from cooperating with the piston, and a second extreme position, in which the dose setting member is prevented from being operated to set a dose,
 wherein the mode locking means is adapted to be in the first extreme position during dose setting and in the second extreme position during injection of a set dose.

In the present context the term 'housing' should be interpreted to mean a part which at least substantially encloses the remaining parts of the injection device, thereby forming a kind of boundary of the injection device. The housing may be provided with one or more completely closed walls or wall parts, and/or it may be provided with one or more relatively open walls or wall parts, e.g. in the form of a grid.

The dose setting member is a part of the injection device which the user operates manually in order to set a desired dose. This will be explained further below.

The piston is preferably positioned inside a cartridge containing a relevant liquid drug. The piston rod and the piston are preferably positioned in abutment with each other in such a manner that moving the piston rod in a distal direction will cause the piston to be moved in a distal direction, thereby pushing liquid drug out of the cartridge. The cartridge may form part of the injection device. In this case the injection device is of the kind which is delivered with the liquid drug already present in the injection device, and when this drug has been delivered, the injection device is discarded. Alternatively, the cartridge may be a separate, removable part. In this case an empty cartridge, and optionally one or more additional parts, can be replaced by a new cartridge, i.e. only the empty cartridge, and optionally the additional part(s), is discarded while the injection device is reused.

The injection device may be of a kind in which energy is stored in a spring member during dose setting. Subsequently, during injection, the stored energy is released and used for driving the piston rod, thereby causing a set dose to be expelled from the injection device. Such an injection device has the advantage that it is easy to use for persons having poor dexterity or low finger strength, since the user does not have to provide the force needed to cause the set dose to be expelled from the injection device.

Alternatively, the injection device may be of a manually operable kind, where the user has to provide the force needed to expel a set dose from the injection device, or it may be of a motor driven kind.

The mode locking means is adapted to be in a first extreme position and in a second extreme position. When the mode locking means is in the first extreme position the piston rod is prevented from cooperating with the piston. Accordingly, the piston can not be accidentally moved when the mode locking means is in the first extreme position, and thereby liquid drug can not be accidentally spilled. Furthermore, it is prevented that a gap may form between the piston and the piston rod, and thereby the risk of sucking blood into the cartridge when the injection needle is subsequently inserted at the injection site, is minimised. Since the mode locking means is adapted to be in the first extreme position during dose setting, the mode locking means prevents undesired spilling of liquid drug, as well as undesired blood in the cartridge, during dose setting.

On the other hand, when the mode locking means is in the second extreme position the dose setting member is prevented from being operated to set a dose. Accordingly, the dose setting member can not be accidentally operated when the mode locking means is in the second extreme position. Since the mode locking means is adapted to be in the second extreme position during injection of a set dose, it is thereby prevented that an initially set dose is accidentally increased or decreased during injection. Thereby it is ensured that the dose which is actually injected is in fact the initially set, desired dose.

Thus, the mode locking means locks the piston rod during dose setting and the dose setting means during injection of a set dose.

The mode locking means does not form part of a cylindrical scale drum, neither is the operation of the mode locking means dependent on the movements of such a scale drum.

Accordingly, it is possible to apply the mode locking means to injection devices where a cylindrical scale drum for some reason has been omitted.

Thus, a mechanically simple solution to the above problem has been provided. Furthermore, the present invention provides the possibility of producing a relatively flat injection device having a mode locking mechanism, since the mode locking mechanism can be provided at a relatively small diameter. This is very advantageous.

In one embodiment the piston rod may be prevented from moving in a distal direction when the mode locking means is in the first extreme position. If the injection device has an elongated shape, i.e. if the injection device is a so-called 'pen-shaped' injection device, the piston rod is normally a relatively stiff elongated member mounted in the injection device in such a manner that it may perform substantially linear movements along its longitudinal axis. Furthermore, the piston rod is mounted in such a manner that linear movements of the piston rod in a distal direction, i.e. towards the position of a mounted injection needle, causes a corresponding movement in the distal direction of the piston in the cartridge, and thereby expelling of liquid drug from the injection device. The injection device is further provided with manually operable injection means, e.g. in the form of an injection button. After a desired dose has been set the user operates the injection means, e.g. pushing an injection button. This causes a movement of the piston rod in a distal direction and by an amount corresponding to the set dose. Thereby the set dose is injected by the injection device.

Alternatively or additionally, the dose setting member may be rotationally operable to set a desired dose, and the dose setting member may be prevented from performing a rotational movement when the mode locking means is in the second extreme position. In this case the dose setting member may be in the form of a rotational dose knob which can be manually dialled in order to set a desired dose. Dialling the dose setting member preferably causes an injection button to be moved at least substantially linearly out of the housing in a proximal direction, i.e. in a direction away from the position of the injection needle. The set dose is preferably displayed, e.g. on an electronic display mounted on the housing. Preventing the dose setting member from performing a rotational movement, thus, prevents the dose setting member from being operated to set a dose, including changing a previously set dose, during injection.

The dose setting member may, e.g., be prevented from performing a rotational movement by means of engaging sets of teeth provided on the mode locking means and on the dose setting member, and the sets of teeth may be moved into engagement when the mode locking means is moved into the second extreme position. Alternatively, the dose setting member may be prevented from performing a rotational movement due to abutment between mating surfaces, or this feature may be provided in any other suitable manner and using any other suitable means.

The mode locking means may further be adapted to be in an intermediate position in which the piston rod is prevented from cooperating with the piston, and the dose setting member is prevented from being operated to set a dose, and the mode locking means may be adapted to be in the intermediate position when being moved between the first and the second extreme positions. Thus, when the mode locking means is in the intermediate position, movement of the piston rod as well as operation of the dose setting means is prevented. Accordingly, when the mode locking means is moved between the first and the second extreme positions, the piston rod can not be accidentally moved, and the dose setting means can not be accidentally operated. Thereby the first and second extreme positions are well separated in the sense that there is no overlap at all between the two extreme positions, i.e. it will not be possible for the mode locking means to be in a position where it is possible for the piston rod to cooperate with the piston while it is also possible to operate the dose setting member to set a dose. This is very advantageous.

According to one embodiment the mode locking means may be provided with a first set of teeth, and the piston rod may be operatively connected to a dosing member, the dosing member being provided with a first set of mating teeth, and the first set of teeth and the first set of mating teeth may engage when the mode locking means is in the first extreme position. The operative connection between the piston rod and the dosing member may preferably be provided by means of a dose rod, preferably in the following manner. The piston rod may be engaging the dose rod via a first thread, and the dose rod may further be engaging the dosing member via a second thread having the same pitch as the first thread. In this case the dosing member ensures that the dose rod is rotated in a controlled manner which prevents the piston rod from moving during dose setting. On the other hand when the mode locking means is in the second extreme position, i.e. during injection, the first set of teeth and the first set of mating teeth preferably do not engage. Accordingly, in this situation the dosing member will be able to rotate, and it will be caused to do so due to the dose rod advancing axially, but being prevented from rotating.

Thus, when the first set of teeth and the first set of mating teeth engage, the dosing member is prevented from performing a rotational movement relatively to the mode locking means. Since the piston rod and the dosing member are operatively connected, the piston rod is thereby prevented from being operated via the dosing member.

Alternatively or additionally, the mode locking means may be provided with a second set of teeth, and the dose setting member may be provided with a second set of mating teeth, and the second set of teeth and the second set of mating teeth may engage when the mode locking means is in the second extreme position. As described above, the dose setting member will be prevented from performing a rotational movement when the second set of teeth and the second set of mating teeth engage. In the case that the dose setting member is rotationally operable to set a dose, the engagement thereby prevents the dose setting member from being operated to set a dose.

The mode locking means may be rotationally locked to the housing, i.e. the mode locking means may be prevented from performing rotational movements relatively to the housing. Alternatively, the mode locking means may be allowed to rotate relatively to the housing if the mode locking means is instead rotationally locked to one or more elements of the injection device performing 'reversible movements' during dose setting and injection, respectively. In the present context the term 'reversible movement' should be understood as a movement which rotates the relevant element relatively to the housing through a specific angle and in a specific direction during dose setting, and through the same angle in the opposite direction during injection. Thus, the relevant element, and thereby the mode locking means, is always returned to the initial angular position.

The injection device may further comprise an injection button being operable to cause the piston rod to cooperate with the piston to cause a set dose to be expelled from the injection device, the injection button being operatively connected to the mode locking means in such a manner that when the injection button is operated to cause a set dose to be expelled from the injection device, the mode locking means is automatically moved from the first extreme position to the second extreme position. According to this embodiment the injection device is preferably operated in the following manner.

When it is desired to inject a dose of liquid drug the user sets the desired dose by manually operating the dose setting member. It may be necessary to manually move the mode locking means into the first extreme position prior to setting the dose. When the desired dose has been set, the injection needle is inserted in a desired injection position, and subsequently the injection button is operated. Initially, this operation will result in the mode locking means being moved from the first extreme position to the second extreme position, preferably via an intermediate position as described above. When the mode locking means has been moved into the second extreme position it will be possible to operate the piston rod, and further operation of the injection button will therefore cause the set dose to be expelled from the injection device.

According to a preferred embodiment, the mode locking means may be adapted to be operated independently of a cylindrical scale drum. Thereby it is possible to apply the mode locking feature in an injection device which does not comprise such a cylindrical scale drum.

BRIEF DESCRIPTION OF THE DRAWINGS

The invention will now be described in further details with reference to the accompanying drawings in which.

DETAILED DESCRIPTION OF THE DRAWINGS

Figure 1:
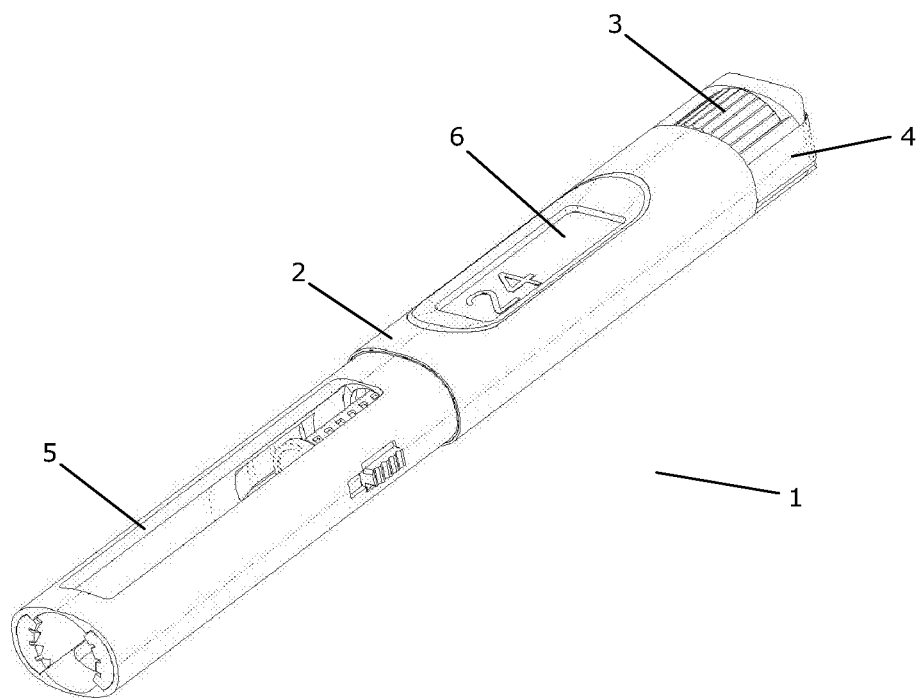
FIG. 1 is a perspective view of an injection device according to a first embodiment of the invention.

FIG. 1 is a perspective view of an injection device 1 comprising a housing 2, a dose setting member 3 which is rotationally operable to set a desired dose, and an injection button 4 which is manually operable to cause a set dose to be expelled from the injection device 1. The housing 2 comprises a cartridge holding part 5 being adapted to accommodate a cartridge containing a liquid drug to be injected by means of the injection device 1. The injection device 1 is further provided with a display 6 adapted to display various relevant information, including the size of a dose being set.

Figure 2:
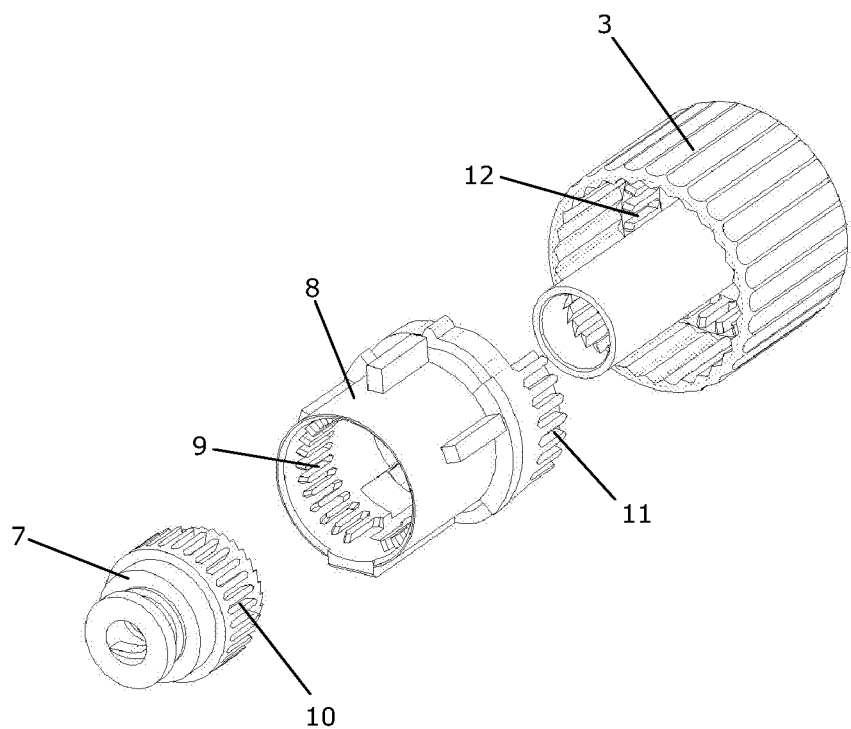
FIG. 2 shows a dosing member, a mode locking member and a dose setting member for use in the injection device of FIG. 1, FIGS. 3-6 show selected parts of the injection device of FIG. 1 at various positions during operation of the injection device.

FIG. 2 shows a dosing member 7, a mode locking member 8 and a dose setting member 3 for use in the injection device of FIG. 1. The inner surface of the mode locking member 8 is provided with a first set of teeth 9, and the outer surface of the dosing member 7 is provided with a first set of mating teeth 10. The dosing member 7 and the mode locking member 8 may be positioned relatively to each other in such a manner that the first set of teeth 9 and the first set of mating teeth 10 engage, thereby rotationally locking the dosing member 7 and the mode locking member 8 to each other. This defines a first extreme position for the mode locking member 8. This will be described in further detail below.

Furthermore, the outer surface of the mode locking member 8 is provided with a second set of teeth 11, and the inner surface of the dose setting member 3 is provided with a second set of mating teeth 12. The mode locking member 8 and the dose setting member 3 may be positioned relatively to each other in such a manner that the second set of teeth 11 and the second set of mating teeth 12 engage, thereby rotationally locking the mode locking member 8 and the dose setting member 3 to each other. This defines a second extreme position for the mode locking member 8. This will be described in further details below.

FIGS. 3-6 show selected parts of the injection device 1 of FIG. 1. Thus, for the sake of clarity, only the parts which are essential for illustrating the operation of the injection device 1 are shown in these Figures.

Figure 3:
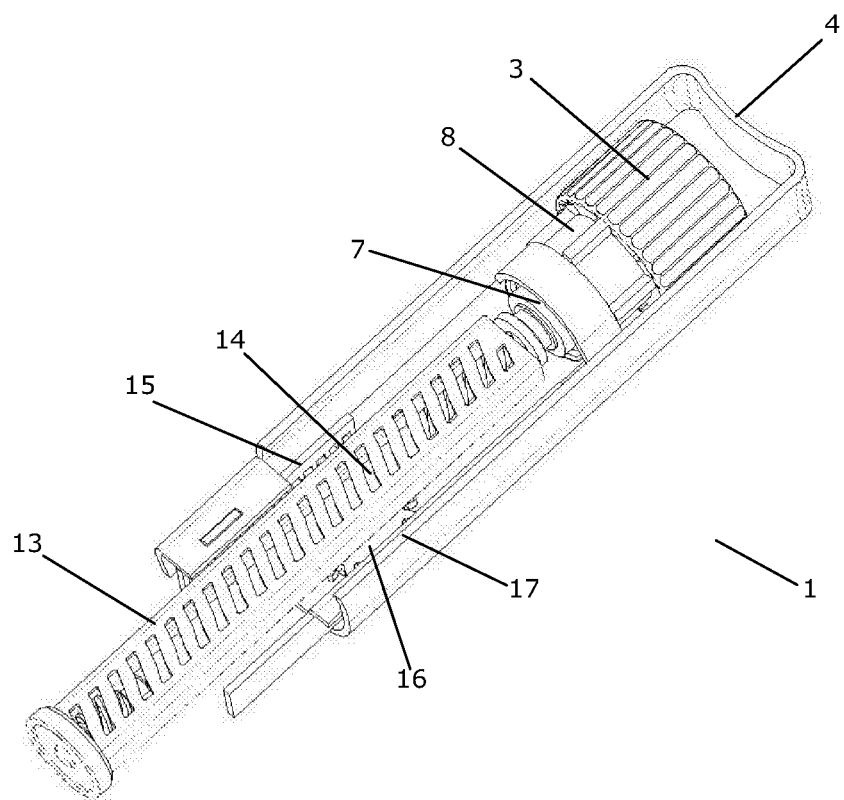

In FIG. 3 the injection device 1 is ready for setting a dose. Thus, the injection button 4 is positioned close to the dose setting member 3 and the mode locking member 8 is positioned in such a manner that the first set of teeth and the first set of mating teeth engage as described above, i.e. the mode locking member 8 is in the first extreme position. The mode locking member 8 is rotationally fixed relatively to the housing, and the dosing member 7 is therefore also rotationally fixed relatively to the housing in the situation illustrated in FIG. 3. A piston rod 13 is positioned relatively close to the position of the dose setting member 3, thereby indicating that the cartridge (not shown) inserted in the injection device 1 is full or almost full.

The dosing member 7 is connected to a dose rod 14 via a first thread, and the dose rod 14 is also connected to the piston rod 13 via a second thread. The first thread and the second thread, in this example, have identical pitch. Accordingly, when the dose setting member 3 is rotated, the dose rod 14 is rotated along in a controlled manner preventing the piston rod 13 from moving during dose setting. During injection the dose rod 14 is moving axially, but is prevented from rotating, since the mode locking member 8 in this situation is in its second extreme position, and thereby the dosing member 7 and the mode locking member 8 are disengaged. Accordingly, since, in the situation illustrated in FIG. 3, the dosing member 7 is prevented from rotating, the piston rod 13 is prevented from moving axially, and it is thereby prevented from pushing the piston in the cartridge, and thereby from causing liquid drug to be expelled from the injection device 1.

When a dose is to be set, the user rotates the dose setting member 3. The dose setting member 3 is operatively connected to the dose rod 14 in such a manner that rotating the dose setting member 3 causes the dose rod 14 to rotate. This will cause the dose rod 14 to move along the piston rod 13, due to the thread. The dose rod 14 is axially connected to a gearwheel 16 via a gearwheel slider (18 in FIG. 7, not visible in FIG. 3). The gearwheel 16 is, via its teeth, engaged with a first rack 15 forming part of the injection button 4. Due to the connection between the dose rod 14 and the gearwheel 16 via the gearwheel slider, the gearwheel 16 is moved axially in a proximal direction when the dose rod 14 is rotated as described above. The gearwheel 16 is also, via its teeth, engaged with a second rack 17 which is operatively connected to the mode locking member 8. Due to this engagement the gearwheel 16 is caused to rotate when it is moved axially along with the dose rod 14. As a result, the injection button 4 is moved axially in a proximal direction with a gearing ration of 2:1, partly due to the axial movement of the gearwheel 16, and partly due to the movement of the first rack 15 as a consequence of the rotation of the gearwheel 16.

Figure 4:
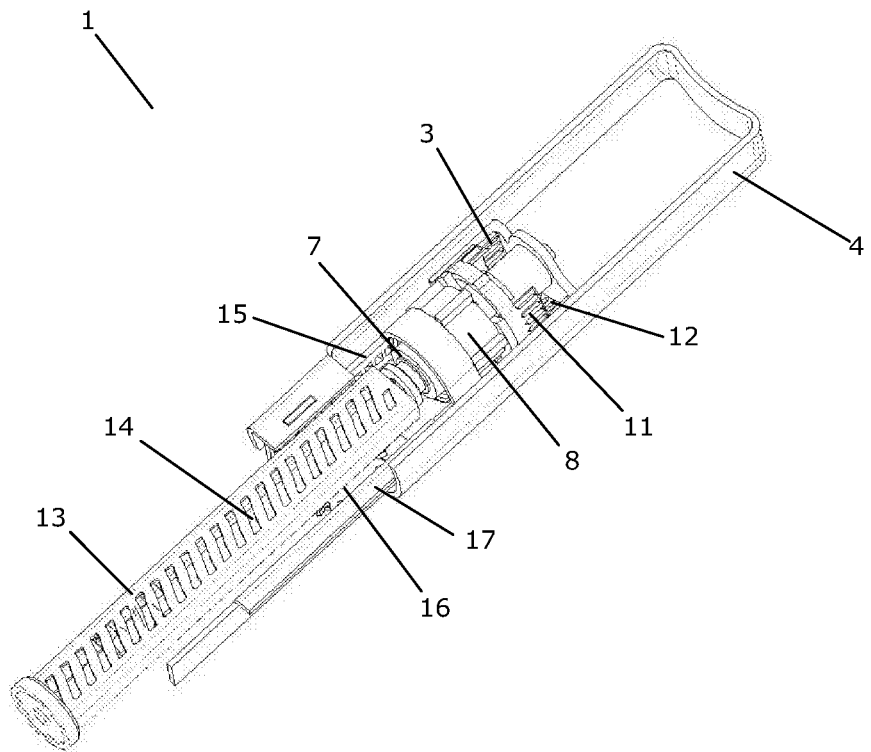

FIG. 4 shows the injection device 1 in a position where a dose has been set. It is clear that the injection button 4 has been moved in a proximal direction as compared to the situation illustrated in FIG. 3. In FIG. 4 the dose setting member 3 is shown with a part broken away in order to illustrate the relative position between the dose setting member 3 and the mode locking member 8. As can be seen, the second set of teeth 11 and the second set of mating teeth 12 do not engage in FIG. 4. Accordingly, it is possible to rotate the dose setting member 3, i.e. it is still possible to increase or decrease the set dose.

In order to inject the set dose, the user will position the injection needle (not shown) at a desired injection site. The user will then push the injection button 4 in order to return it to the position shown in FIG. 3, thereby injecting the set dose. However, as described above the first set of teeth (not shown) engage the first set of mating teeth (not shown), and the dosing member 7 is therefore prevented from performing a rotating movement. Pushing the injection button 4 will therefore not immediately result in the set dose being injected. Instead the following happens.

As mentioned above, the injection button 4 is provided with a first rack 15 which is engaging the gearwheel 16. Accordingly, pushing the injection button 4 will cause the gearwheel 16 to rotate. The gearwheel 16 is further engaging a second rack 17 which, as mentioned above, is operationally coupled to the mode locking member 8. Accordingly, rotating the gearwheel 16 causes the second rack 17, and thereby the mode locking member 8, to move in a proximal direction. Thereby the second set of teeth 11 and the second set of mating teeth 12 are moved into engagement while the first set of teeth 9 and the first set of mating teeth 10 are moved out of engagement, i.e. the mode locking member 8 is moved from the first extreme position to the second extreme position.

Figure 5:
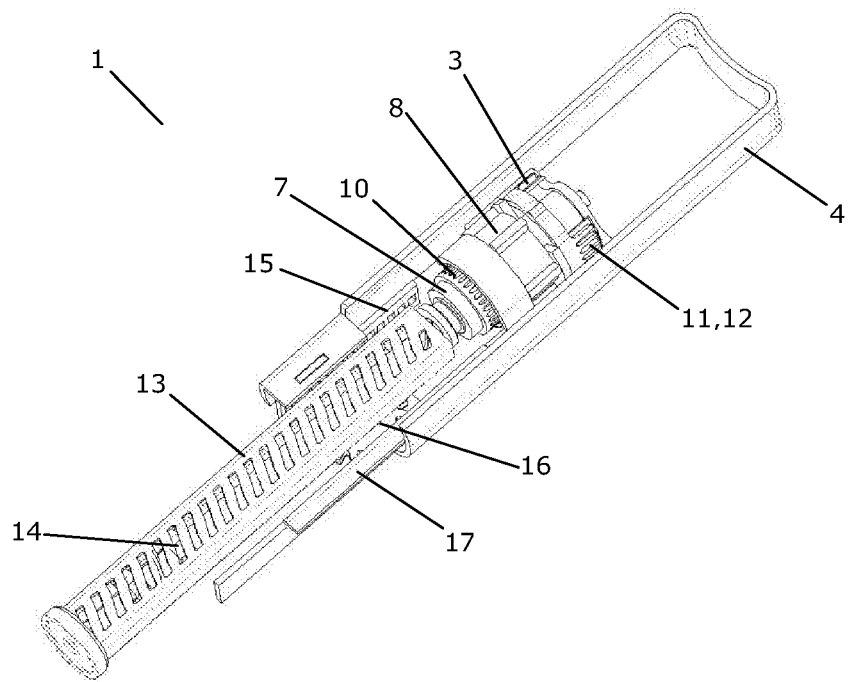

This situation is illustrated in FIG. 5. It is clear that the second set of teeth 11 and the second set of mating teeth 12 have been moved into engagement, and that the first set of teeth (not visible) and the first set of mating teeth 10 have been moved out of engagement. Accordingly, it is now no longer possible to rotate the dose setting member 3 to increase or decrease the set dose. However, the dosing member 7 is now free to rotate relatively to the mode locking member 8. Accordingly, further pushing of the injection button 4 will result in the gearwheel 16 performing a rotational movement and an axial movement in a distal direction. As a consequence the dose rod 14 and the piston rod 13 will move as described above. Since the dose rod 14 is now unable to rotate, it will cause the dosing member 7 to rotate due to the engaging thread. Thereby the dosing member 7 will produce a clicking sound in cooperation with a non-rotating, axially spring loaded second dosing member (not shown).

The above procedure can be performed without the risk of accidentally rotating the dose setting member 3, i.e. it is ensured, due to the engagement of the second set of teeth 11 and the second set of mating teeth 12, that the initially set dose can not be accidentally increased or decreased during injection.

Figure 6:
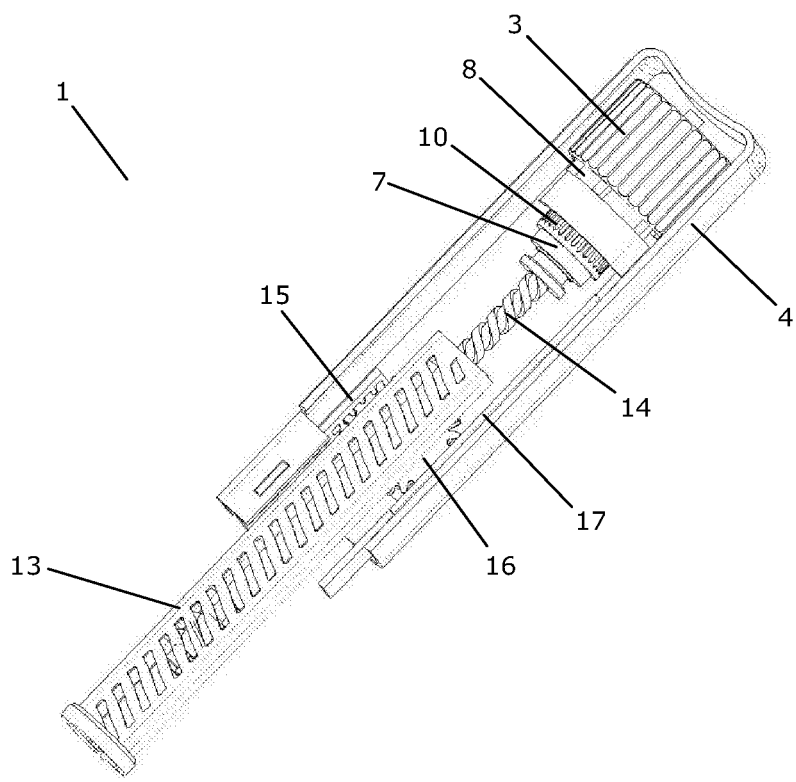

FIG. 6 shows the injection device 1 in a position where the set dose has been injected. Thus, the injection button 4 has returned to the position of FIG. 3. As compared to FIG. 3 the dose rod 14 has been moved in the distal direction, thereby indicating that the piston in the cartridge has been moved correspondingly, and that the set dose has thereby been injected, and that the cartridge is no longer full. It is clear from FIG. 6 that the mode locking member 8 remains in the second extreme position, i.e. the second set of teeth and the second set of mating teeth are kept in engagement. Accordingly, the mode locking member 8 will have to be moved manually to the first extreme position before the injection device 1 is once again ready for setting a new dose.

Figure 7:
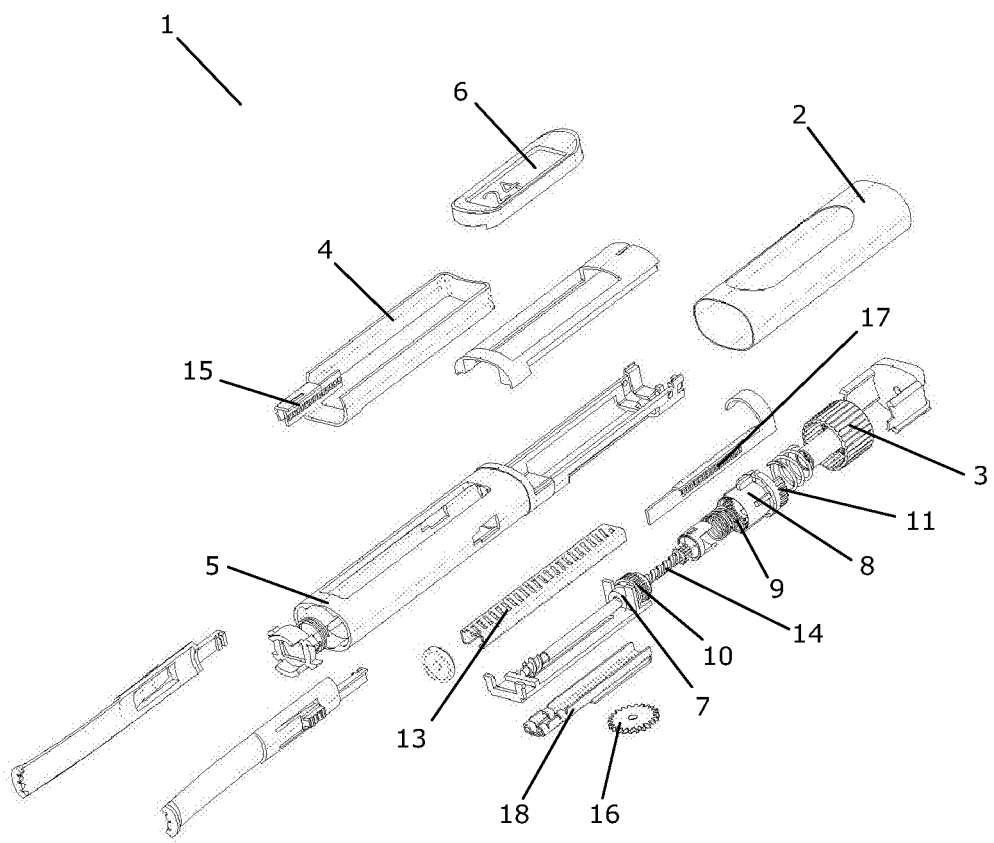
FIG. 7 is an exploded view of the injection device of FIG. 1.

FIG. 7 is an exploded view of the injection device of FIG. 1. Accordingly, FIG. 7 gives a clear view of the individual parts of the injection device 1.

Figure 8:
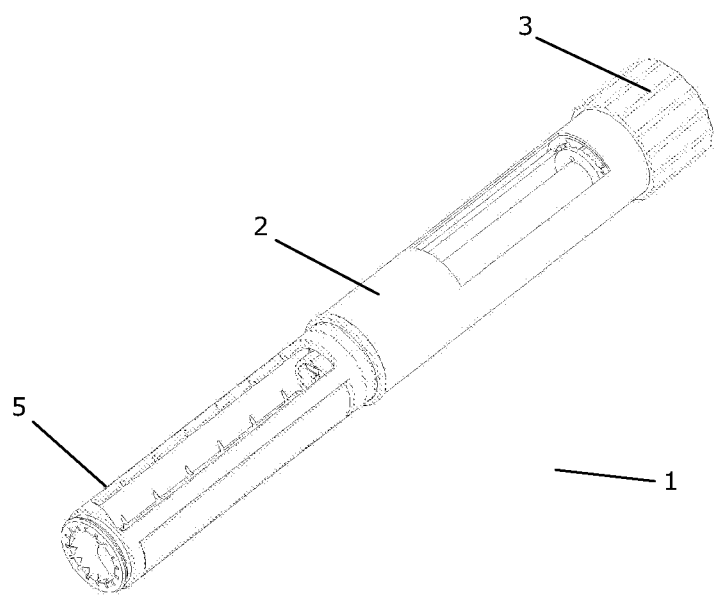
FIG. 8 is a perspective view of an injection device according to a second embodiment of the invention.

FIG. 8 is a perspective view of an injection device 1 according to a second embodiment of the invention, the injection device 1 comprising a housing 2 and a dose setting member 3 which is rotationally operable to set a desired dose. The dose setting member 3 also functions as an injection button. This will be described in further detail below. The housing 2 comprises a cartridge holding part 5 being adapted to accommodate a cartridge containing a liquid drug to be injected by means of the injection device 1. The injection device 1 is of the kind in which energy is stored in a spring member during dose setting, the energy being released during injection and used for driving a piston rod in order to cause a set dose to be expelled from the injection device 1. This will also be explained further below.

Figure 9:
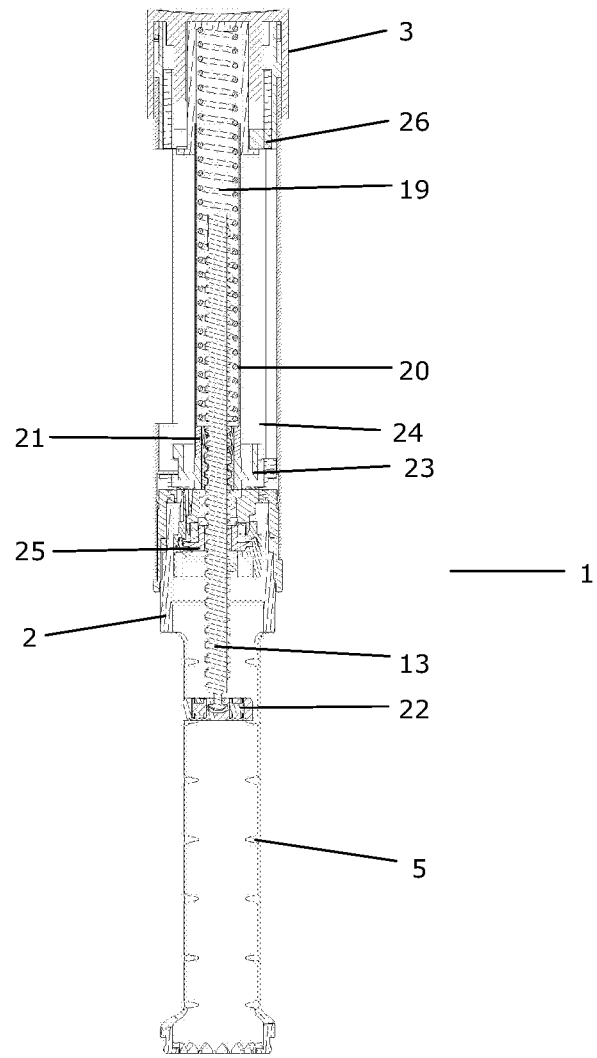
FIG. 9 is a cross sectional view of the injection device of FIG. 8, FIGS. 10-13 show selected parts of the injection device of FIG. 8 at various positions during operation of the injection device.

FIG. 9 is a cross sectional view of the injection device 1 of FIG. 8. In FIG. 9 a piston rod 13 and a compressible spring 19 are visible. The compressible spring 19 is arranged inside a dosage tube 20, and it is compressed during dose setting by means of spring compressing member 21 attached at the interior of the dosage tube 20. Thereby energy is stored in the compressible spring 19, and this energy is released during injection and used for driving the piston rod 13 in a distal direction, thereby pushing a piston 22 arranged inside a cartridge (not shown) in a distal direction and causing a set dose to be expelled from the injection device 1.

During dose setting the piston rod 13 is prevented from moving in a distal direction in the following manner. A set of teeth arranged on a first locking member 23, being threadedly engaged with the piston rod 13, engages a set of teeth arranged on a tube 24 which is rotationally locked to the housing 2. The first locking member 23 and the tube 24 are thereby prevented from performing relative rotation. At the same time, rotary lock 25 prevents the piston rod 13 from rotating. Thereby the piston rod 13 is prevented from moving in a distal direction. This will be explained in further detail below with reference to FIGS. 10-13.

During injection the dose setting member 3 is prevented from performing rotational movement because a set of teeth arranged on a second locking member 26, being rotationally locked relatively to the housing 2, engages a set of teeth arranged in the interior of the dose setting member 3. This will also be explained in further detail below.

FIGS. 10-13 show selected parts of the injection device 1 of FIG. 8. Thus, for the sake of clarity, only the parts which are essential for illustrating the operation of the injection device 1 are shown in these Figures.

Figure 10:
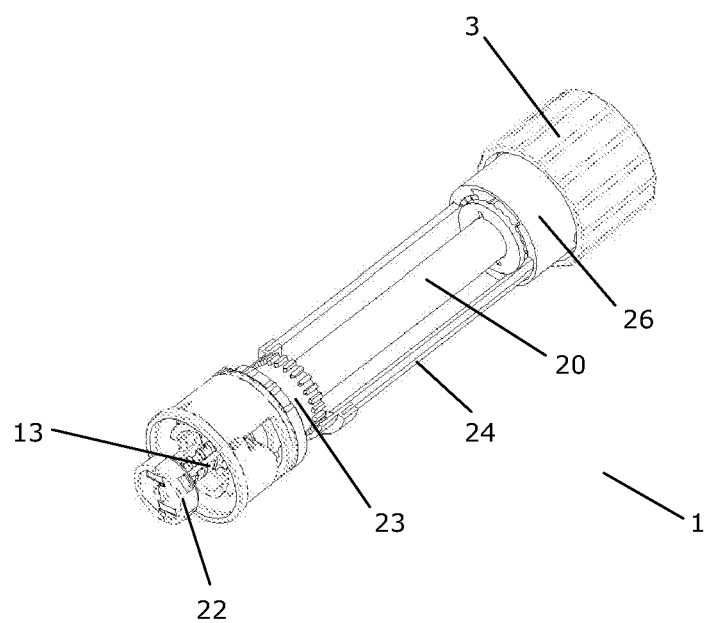

In FIG. 10 the injection device 1 is ready for setting a dose. It can be seen that the teeth arranged on the first locking member 23 engages the teeth arranged on the tube 24. Due to this engagement, and since the piston rod 13 is threadedly engaged to the first locking member 23, it will only be allowed to move in a distal direction if it spirals through the first locking member 23. However, as described above, the piston rod 13 is prevented from performing rotational movement due to the rotary lock (not visible in FIG. 10). Accordingly, the piston rod 13 is prevented from moving in a distal direction.

When it is desired to set a dose, the dose setting member 3 is dialled, thereby rotating dosage tube 20 and spring compressing member (not visible) arranged inside dosage tube. This causes the spring compressing member (not visible) to climb the thread of the piston rod 13, thereby compressing the spring (not visible) and moving the dosage tube 20 in a proximal direction.

Figure 11:
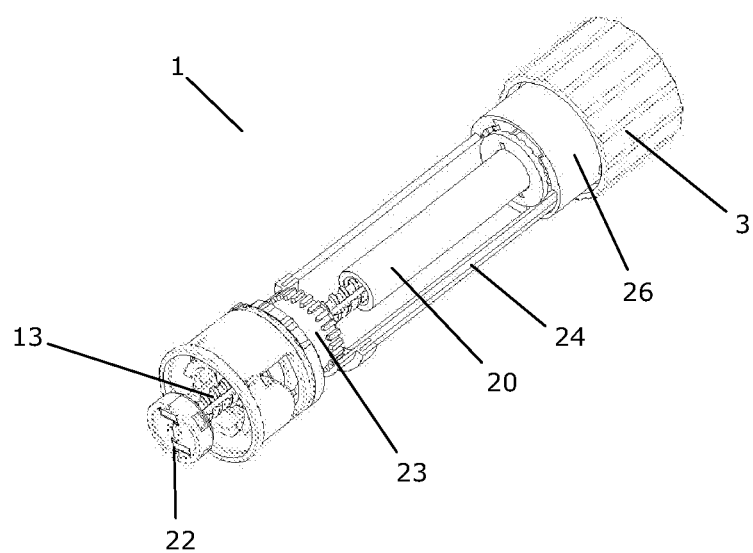

FIG. 11 shows the injection device 1 in a position where a dose has been set. It can be seen that the dosage tube 20 has been moved in a proximal direction. The set of teeth arranged on the first locking member 23 still engages the set of teeth arranged on the tube 24, i.e. the piston rod 13 is still prevented from moving in a distal direction as described above.

When it is desired to inject the set dose, the dose setting member 3 is pushed in a distal direction. Initially, this will push the set of teeth arranged on the second locking member 26 into engagement with the set of teeth arranged in the interior of the dose setting member 3, thereby preventing further rotation of the dose setting member 3, i.e. preventing further setting of the dose. During this initial movement, the set of teeth arranged on the first locking member 23 continues to engage the set of teeth arranged on the tube 24. Thus, during an initial time period the dose setting member 3 will be prevented from rotating while the piston rod 13 will be prevented from moving in a distal direction, i.e. dose setting as well as injection is prevented at the same time. Thereby the risk that dose setting as well as injection is possible at a certain point in time is eliminated.

Pushing the dose setting member 3 further in a distal direction pushes the tube 24 in a distal direction, thereby moving the set of teeth arranged on the tube 24 out of engagement with the set of teeth arranged on the first locking member 23. Thereby the first locking member 23 is allowed to rotate. Accordingly, the piston rod 13 is allowed to move in a distal direction while causing rotation of the first locking member 23. At the same time the energy stored in the spring is released, and the released energy is used for driving the piston rod 13 in a distal direction, thereby causing the set dose to be expelled.

Figure 12:
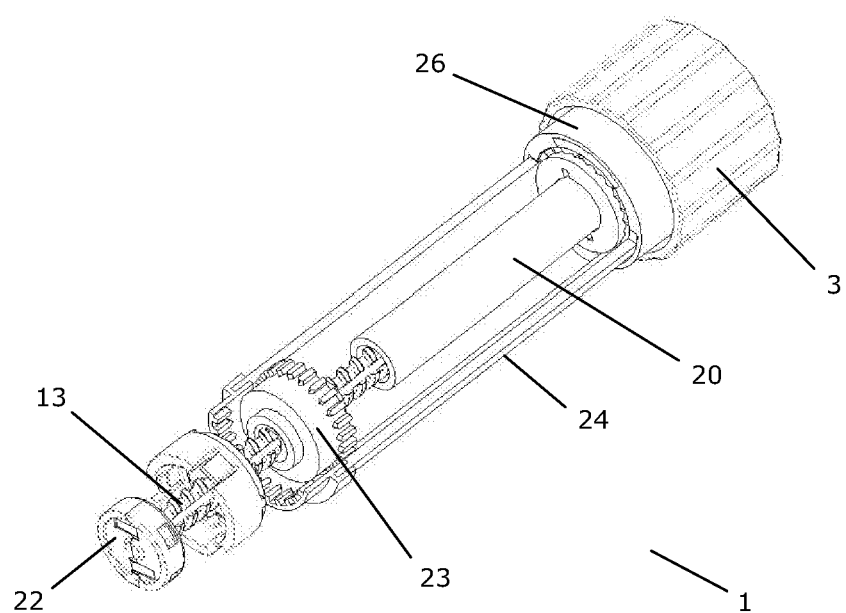

FIG. 12 shows the injection device 1 in a position where the dose setting member 3 has been pushed in a distal direction sufficiently to cause the set of teeth arranged on the second locking member 26 to engage the set of teeth arranged in the interior of the dose setting member 3, and sufficiently to cause the set of teeth arranged on the first locking member 23 to disengage the set of teeth arranged on the tube 24. However, the energy stored in the spring has only just been released, and the piston rod 13 has therefore not yet been moved.

Figure 13:
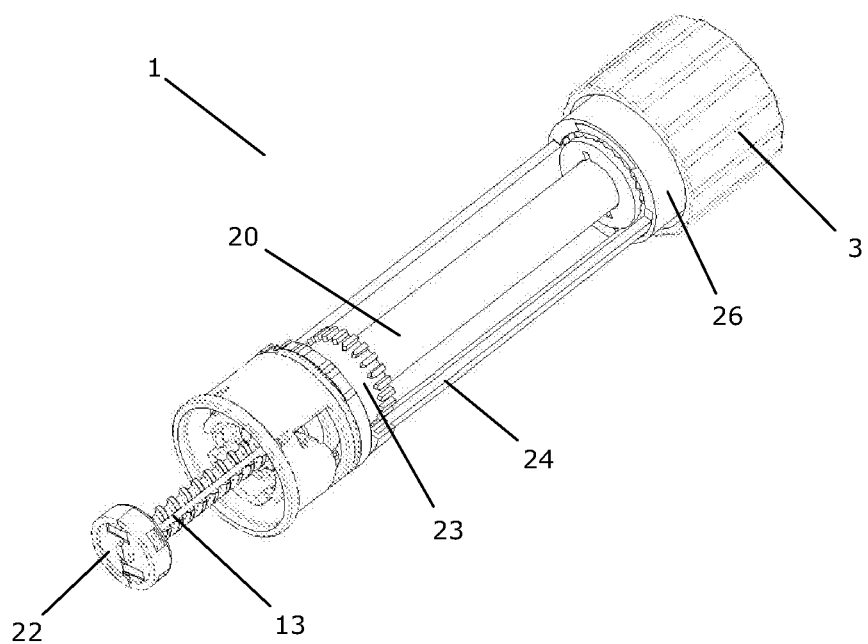

FIG. 13 shows the injection device 1 in a position where the set dose has been injected. Thus, the dosage tube 20 has been moved back to the initial position, and the piston rod 13 has been moved distally. The set of teeth arranged on the first locking member 23 is still out of engagement with the set of teeth arranged on the tube 24, and the set of teeth arranged on the second locking member 26 is still engaging the set of teeth arranged in the interior of the dose setting member 3. However, relieving the pressure on the dose setting member 3 will cause a reversal of this situation.

Figure 14:
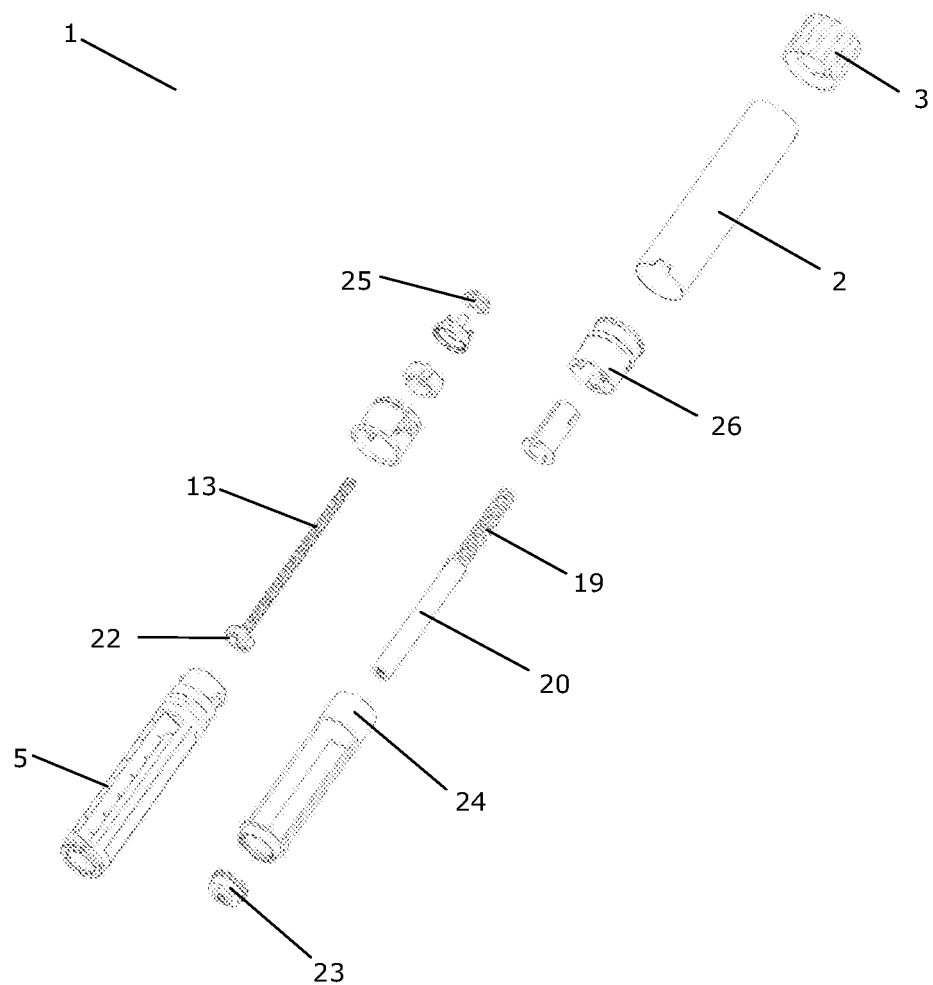
FIG. 14 is an exploded view of the injection device of FIG. 8.

FIG. 14 is an exploded view of the injection device 1 of FIG. 8. Accordingly, FIG. 14 gives a clear view of the individual parts of the injection device 1.

The invention claimed is:
1. An injection device comprising:
a housing,
a dose setting member being rotationally operable to set a desired dose, a piston rod adapted to cooperate with a piston to cause a set dose to be expelled from the injection device, a mode locking member rotationally locked to the housing and movable between a first extreme position during dose setting, and a second extreme position during injection, an injection button operable by pushing to cause the piston rod to cooperate with the piston to cause a set dose to be expelled from the injection device, the injection button being operatively connected to the mode locking member in such a manner that when the injection button is operated by pushing to cause a set dose to be expelled from the injection device, the mode locking member is automatically moved from the first extreme position to the second extreme position, wherein during dose setting the mode locking member in the first extreme position prevents the piston rod from cooperating with the piston by locking the piston rod, wherein during injection the mode locking member in the second extreme position prevents the dose setting member from performing rotational movement and being operated to set a dose.

2. An injection device according to claim 1, wherein the piston rod is prevented from moving in a distal direction when the mode locking member is in the first extreme position.

3. An injection device according to claim 1, wherein the mode locking member is further adapted to be in an intermediate position in which the piston rod is prevented from cooperating with the piston, and the dose setting member is prevented from being operated to set a dose, the mode locking member being adapted to be in the intermediate position when being moved between the first and the second extreme positions.

4. An injection device according to claim 1, wherein the mode locking member is provided with a first set of teeth, and wherein the piston rod is operatively connected to a dosing member, the dosing member being provided with a first set of mating teeth, and wherein the first set of teeth and the first set of mating teeth engage when the mode locking member is in the first extreme position.

5. An injection device according to claim 4, wherein the mode locking member is provided with a second set of teeth, and the dose setting member is provided with a second set of mating teeth, and wherein the second set of teeth and the second set of mating teeth engage when the mode locking member is in the second extreme position.

6. An injection device according to claim 1, wherein the mode locking member is adapted to be operated independently of a cylindrical scale drum.

7. An injection device according to claim 1, further comprising a dosage tube coupled between the dose setting member and the piston rod, wherein the dosage tube is adapted to move along the piston rod during dose setting.

8. An injection device according to claim 1, wherein during dose setting the mode locking member is positioned in the first extreme position relative to the housing and that during injection the mode locking member is positioned in the second extreme position relative to the housing.

9. An injection device comprising:
a housing,
a dose setting member being operable to set a desired dose,
a piston rod adapted to cooperate with a piston to cause a set dose to be expelled from the injection device,
a mode locking member rotationally locked to the housing and movable between a first extreme position during dose setting, and a second extreme position during injection,
an injection button operable by pushing to cause the piston rod to cooperate with the piston to cause a set dose to be expelled from the injection device, the injection button being operatively connected to the mode locking member in such a manner that when the injection button is operated by pushing to cause a set dose to be expelled from the injection device, the mode locking member is automatically moved from the first extreme position to the second extreme position,
wherein during dose setting the mode locking member in the first extreme position prevents the piston rod from cooperating with the piston by locking the piston rod,
wherein the mode locking member (8) and dose setting member (3) are each provided with a set of teeth (11, 12), and
the teeth (11, 12) from the dose setting member and mode locking member engage when the mode locking member is in the second extreme position during injection of a set dose.

10. An injection device according to claim 9, wherein the mode locking member is structured to move relative to the housing.

11. An injection device according to claim 9, further comprising a dosage tube coupled between the dose setting member and the piston rod, wherein the dosage tube is adapted to move along the piston rod during dose setting.

12. An injection device according to claim 9, wherein the piston rod is prevented from moving in a distal direction when the mode locking member is in the first extreme position.

13. An injection device according to claim 9, wherein the mode locking member is further adapted to be in an intermediate position in which the piston rod is prevented from cooperating with the piston, and the dose setting member is prevented from being operated to set a dose, the mode locking member being adapted to be in the intermediate position when being moved between the first and the second extreme positions.

14. An injection device according to claim 9, wherein the mode locking member is provided with a set of teeth (9), wherein the piston rod is operatively connected to a dosing member (7), the dosing member being provided with a set of mating teeth (10), and wherein the set of teeth (9) of the mode locking member (8) and the set of mating teeth (10) of the dosing member (7) engage when the mode locking member is in the first extreme position.

15. An injection device according to claim 14, wherein the dosing member is prevented from rotating when the mode locking member is in the first extreme position and wherein the dosing member is allowed to rotate when the mode locking member is in the second extreme position.

16. An injection device according to claim 15, wherein the dosing member is threadedly connected with the piston rod.

17. An injection device according to claim 15, wherein the piston rod and the dosing member are operatively connected by means of a dose rod.

18. An injection device according to claim 17, wherein the dose setting member is operatively connected to the dose rod so that rotating the dose setting member causes the dose rod to rotate.

19. An injection device according to claim 17, wherein the dose rod engages the piston rod via a first thread and wherein the dose rod is rotated relative to the piston rod during dose setting, wherein the dosing member engages the dose rod via a second thread, and wherein the dosing member is allowed to rotate relative to the mode locking member when the set of teeth (10) of the dosing member (7) and the set of mating teeth (9) of the mode locking member (8) do not engage.

20. An injection device according to claim 19, wherein the pitch of said first thread and the pitch of said second thread are the same.

21. An injection device according to claim 9, wherein the mode locking member is adapted to be operated independently of a cylindrical scale drum.

22. An injection device according to claim 9, wherein during dose setting the mode locking member is positioned in the first extreme position relative to the housing and that during injection the mode locking member is positioned in the second extreme position relative to the housing.

* * * * *